(12) United States Patent
Gozes

(10) Patent No.: US 10,912,819 B2
(45) Date of Patent: Feb. 9, 2021

(54) NEUROPROTECTIVE PEPTIDES DERIVED FROM ACTIVITY-DEPENDENT NEUROPROTECTIVE PROTEIN FOR TREATMENT OF NEUROLOGICAL DISEASES

(71) Applicant: Ramot at Tel-Aviv University Ltd., Tel-Aviv (IL)

(72) Inventor: Illana Gozes, Ramat-Hasharon (IL)

(73) Assignee: Ramot at Tel-Aviv University, Ltd., Tel Aviv (IL)

( * ) Notice: Subject to any disclaimer, the term of this patent is extended or adjusted under 35 U.S.C. 154(b) by 0 days.

(21) Appl. No.: 16/073,199

(22) PCT Filed: Jan. 24, 2017

(86) PCT No.: PCT/IL2017/050087
§ 371 (c)(1),
(2) Date: Jul. 26, 2018

(87) PCT Pub. No.: WO2017/130190
PCT Pub. Date: Aug. 3, 2017

(65) Prior Publication Data
US 2018/0344809 A1 Dec. 6, 2018

Related U.S. Application Data

(60) Provisional application No. 62/288,239, filed on Jan. 28, 2016.

(51) Int. Cl.
| | | |
|---|---|---|
| A61K 38/18 | (2006.01) | |
| A61K 47/10 | (2017.01) | |
| A61K 9/00 | (2006.01) | |
| A61K 9/08 | (2006.01) | |
| A61P 21/00 | (2006.01) | |
| A61P 25/28 | (2006.01) | |
| C12N 15/113 | (2010.01) | |
| C07K 7/08 | (2006.01) | |

(52) U.S. Cl.
CPC ............ *A61K 38/18* (2013.01); *A61K 9/0043* (2013.01); *A61K 9/08* (2013.01); *A61K 47/10* (2013.01); *A61P 21/00* (2018.01); *A61P 25/28* (2018.01); *C12N 15/113* (2013.01); *C07K 7/08* (2013.01)

(58) Field of Classification Search
None
See application file for complete search history.

(56) References Cited

U.S. PATENT DOCUMENTS

| | | | |
|---|---|---|---|
| 5,609,273 A * | 3/1997 | Firestone | A61J 1/00 222/215 |
| 7,452,867 B2 | 11/2008 | Gozes et al. | |
| 7,812,120 B2 | 10/2010 | Quay et al. | |
| 8,067,369 B2 | 11/2011 | Gozes et al. | |
| 8,324,166 B2 * | 12/2012 | Gozes | A61K 38/08 514/17.7 |
| 10,118,943 B2 * | 11/2018 | Gozes | C07K 14/4711 |
| 2007/0185035 A1 | 8/2007 | Costantino | |
| 2012/0142592 A1 * | 6/2012 | Quay | A61K 9/0043 514/11.9 |
| 2015/0141345 A1 * | 5/2015 | Gozes | C07K 14/4711 514/17.7 |
| 2015/0157725 A1 | 6/2015 | Ong et al. | |

FOREIGN PATENT DOCUMENTS

| | | | | |
|---|---|---|---|---|
| EP | 3630340 A1 | 3/1990 | | |
| WO | WO 2013/171595 | * 11/2013 | | C07K 5/103 |

OTHER PUBLICATIONS

Illana Gozes, Pharmacology & Therapeutics, 2007; 114: 146-154 (Year: 2007).*
Illana Gozes, Frontiers in Neuroscience, 2018; 12: 873; doi: 10.3389/fnins.2018.00873; 5 pages total (Year: 2018).*
Kern et al., J Strength Cond Res, 2013; 27: 2277-2281 (Year: 2013).*
Helsmoortel et al., Author Manuscript of Nat Genet. Apr. 2014; 46(4): 380-384. doi:10.1038/ng.2899; 15 pages total (Year: 2014).*
Malishkevich et al., Transl Psychiatry (2015) 5, e501; doi:10.1038/tp.2014.138 (Year: 2015).*
International Search Report in PCT/IL2017/050087, dated May 21, 2017.
Costantino, et al. "Development of calcitonin salmon nasal spray: similarity of peptide formulated in chlorobutanol compared to benzalkonium chloride as preservative." Journal of pharmaceutical sciences 98, No. 10 (2009): 3691-3706.

* cited by examiner

*Primary Examiner* — Christina M Borgeest
(74) *Attorney, Agent, or Firm* — Kilpatrick Townsend & Stockton LLP

(57) ABSTRACT

This invention provides a novel formulation for effective delivery of a pharmaceutically active ingredient such as a peptide possessing neuroprotective activity. Also provided are methods for treating pertinent clinical implications such as autism, schizophrenia, and dementia using the formulation.

13 Claims, 21 Drawing Sheets

Specification includes a Sequence Listing.

Fig. 1A
distribution of NAP labeled with Cy5– whole body scan
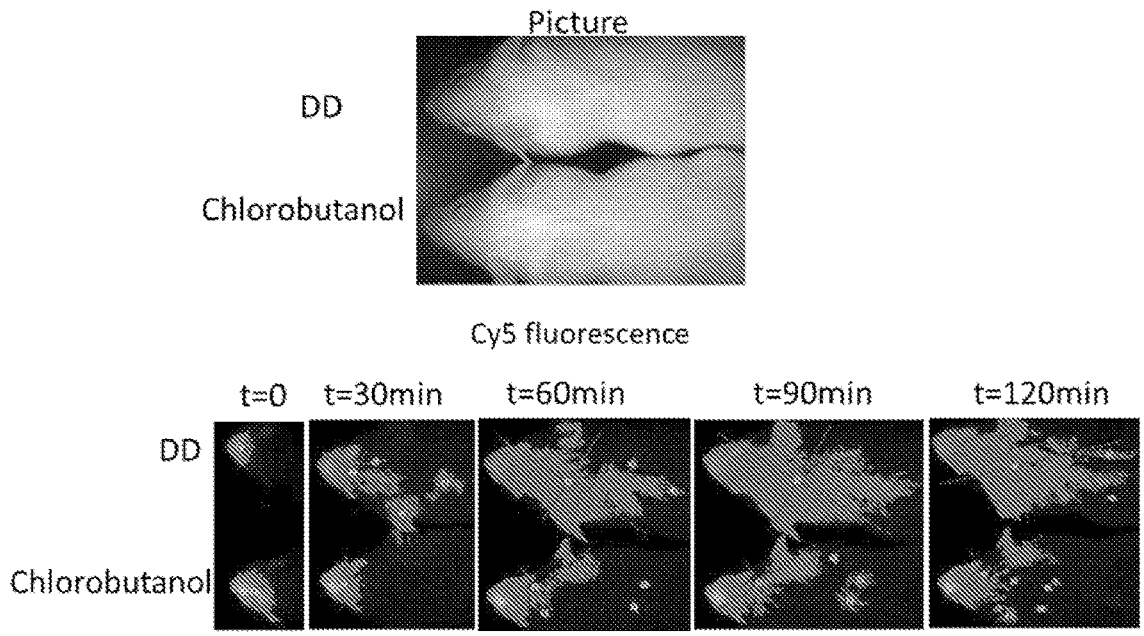
Fig. 1B
distribution of NAP labeled with Cy5– brain
Picture
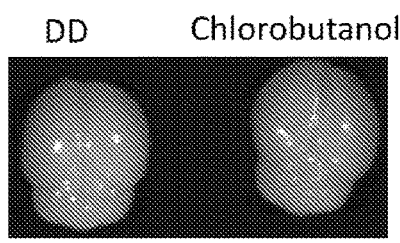
Cy5
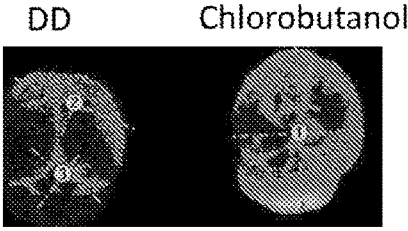

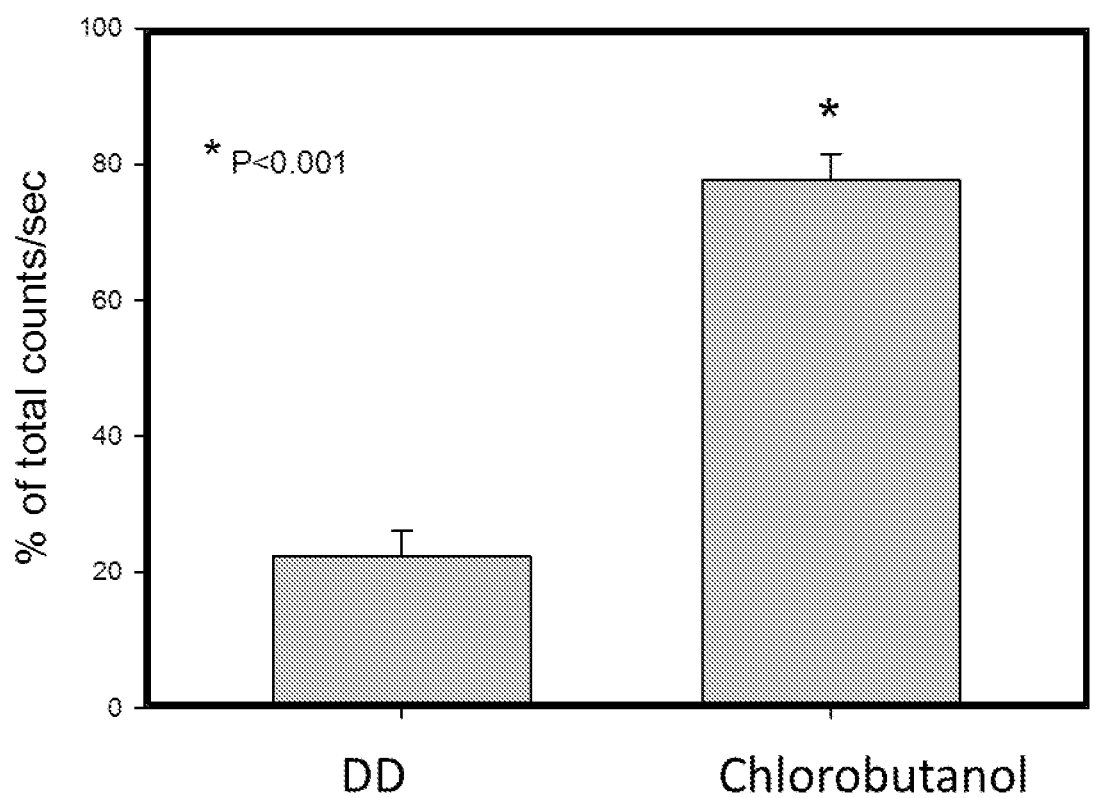

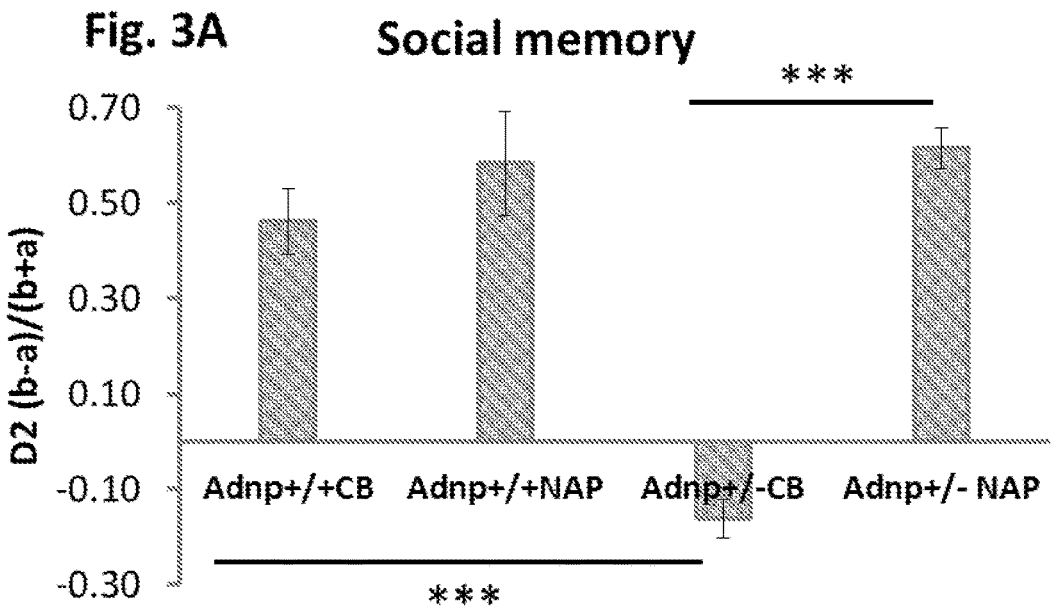
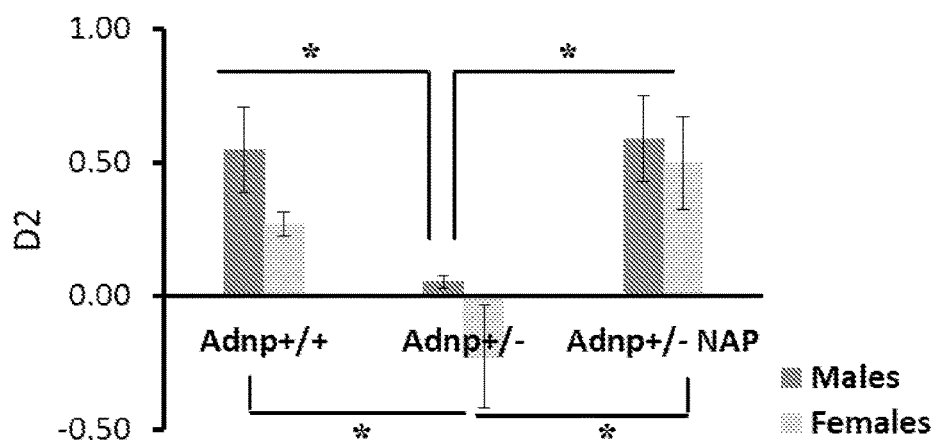
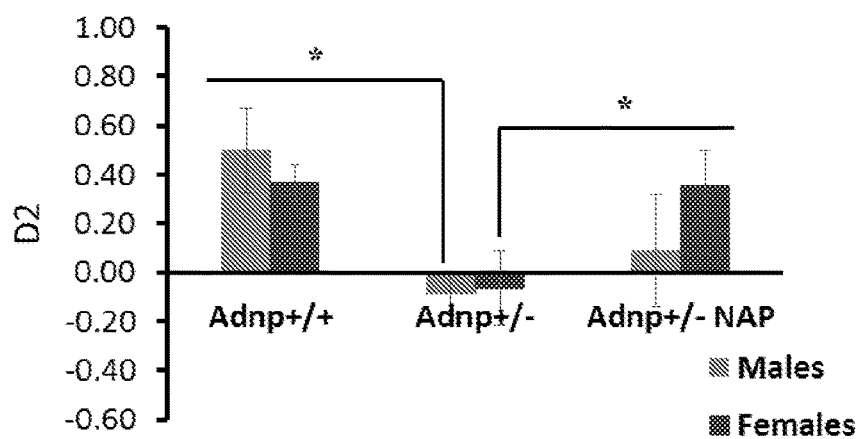

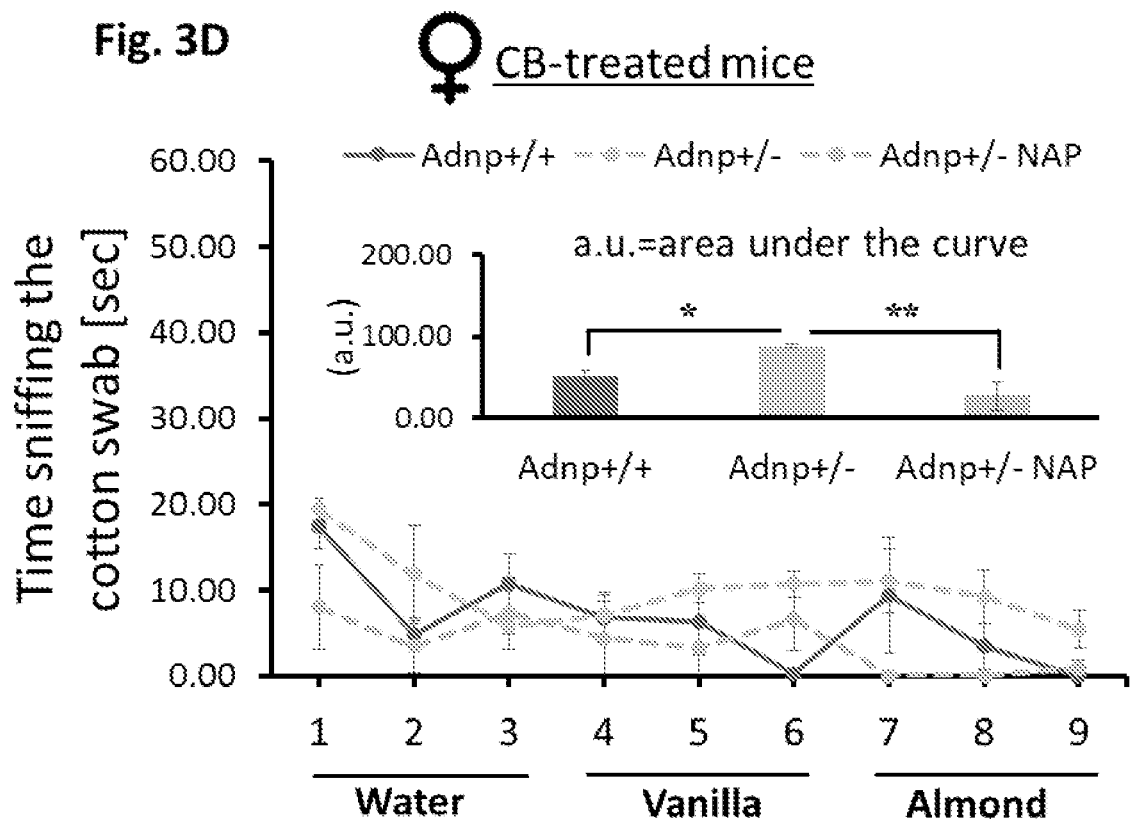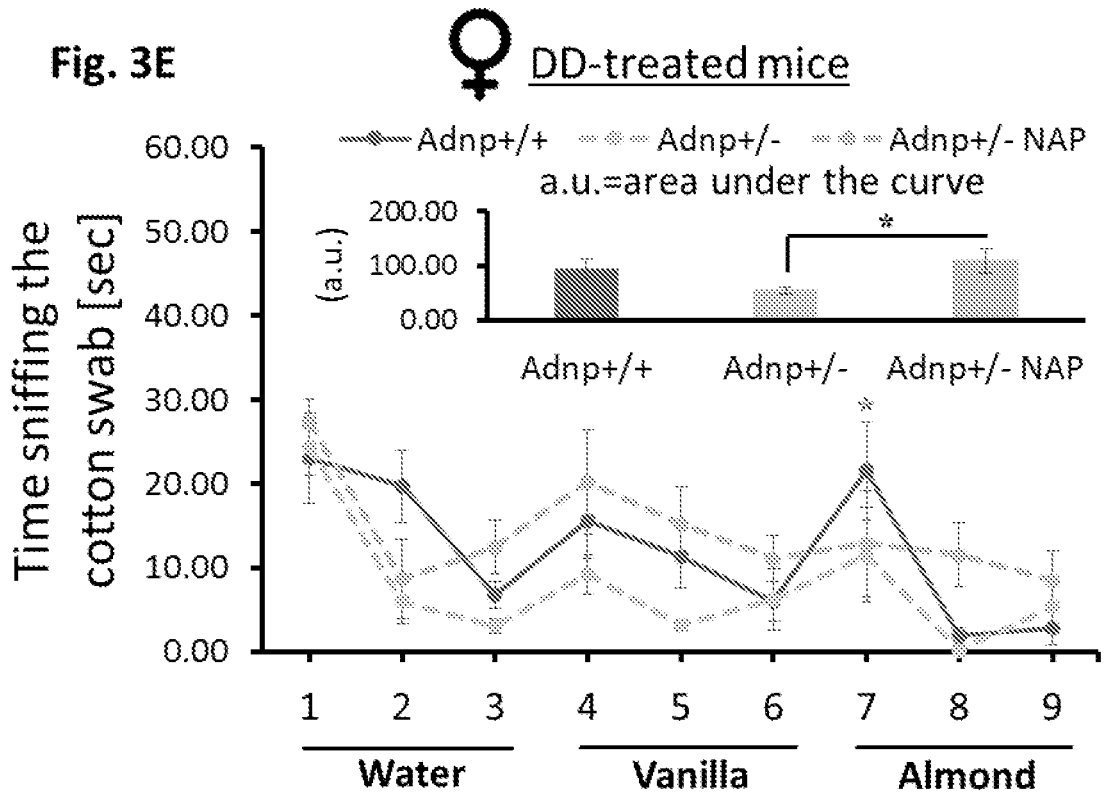

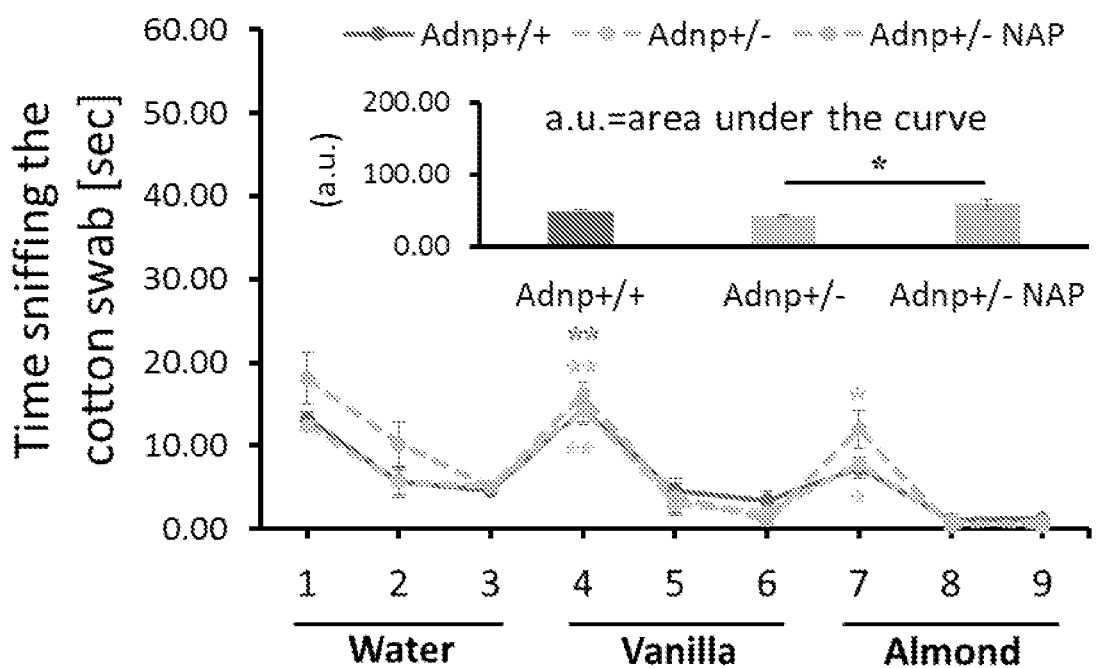
Fig. 3F ♂ CB-treated mice
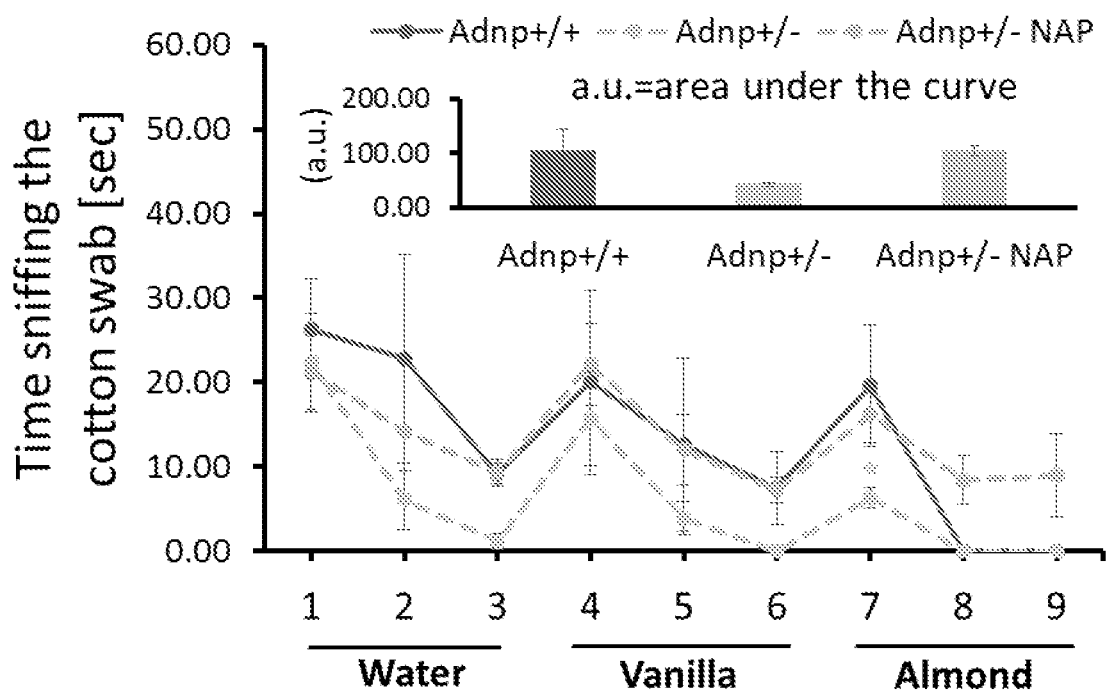
Fig. 3G ♂ DD-treated mice

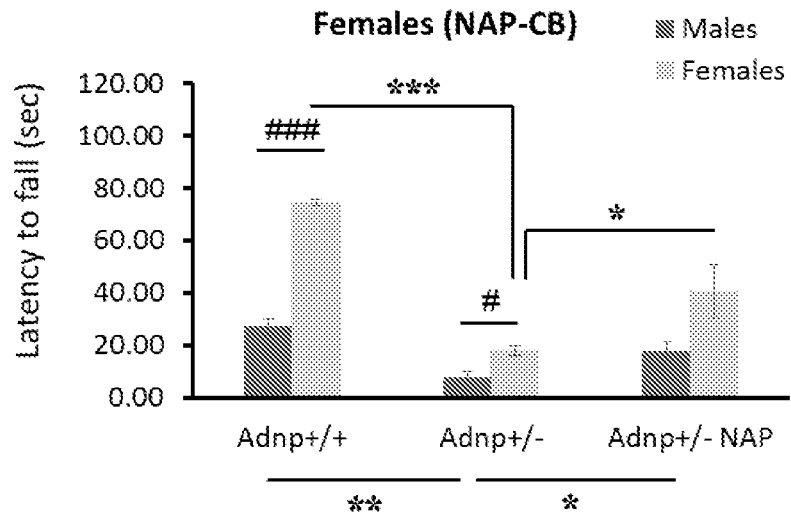
Fig. 5D Hanging wire: 5-month-old Males vs. Females (NAP-CB)
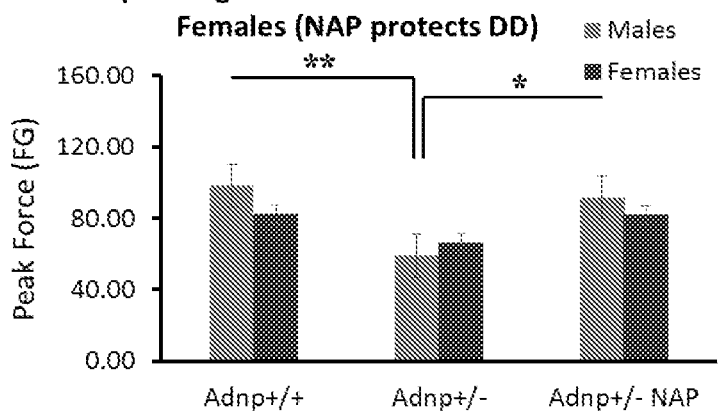
Fig. 5E Grip strength test: 3-month-old Males vs. Females (NAP protects DD)
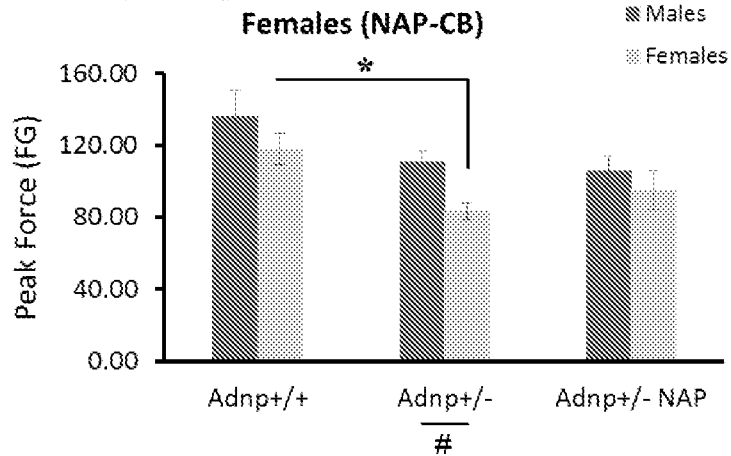
Fig. 5F Grip strength test: 5-month-old Males vs. Females (NAP-CB)

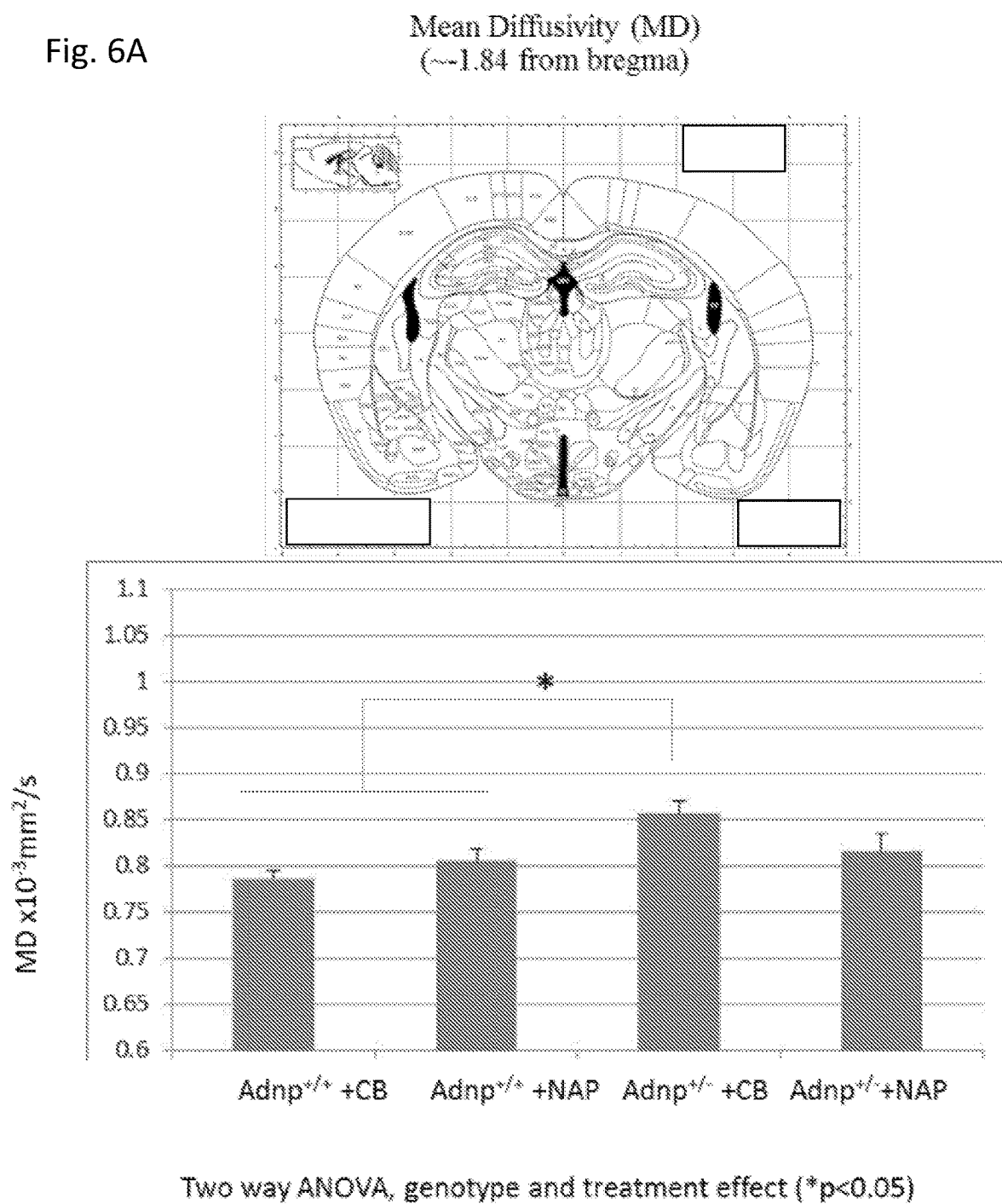

Fig. 6B
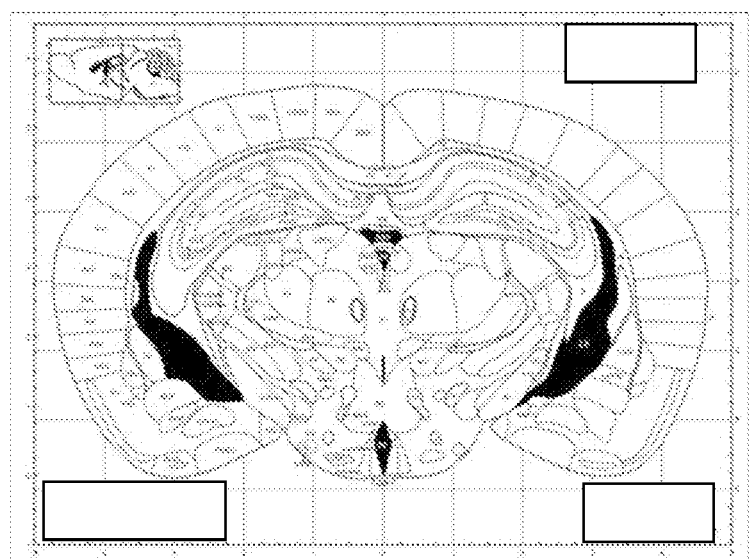
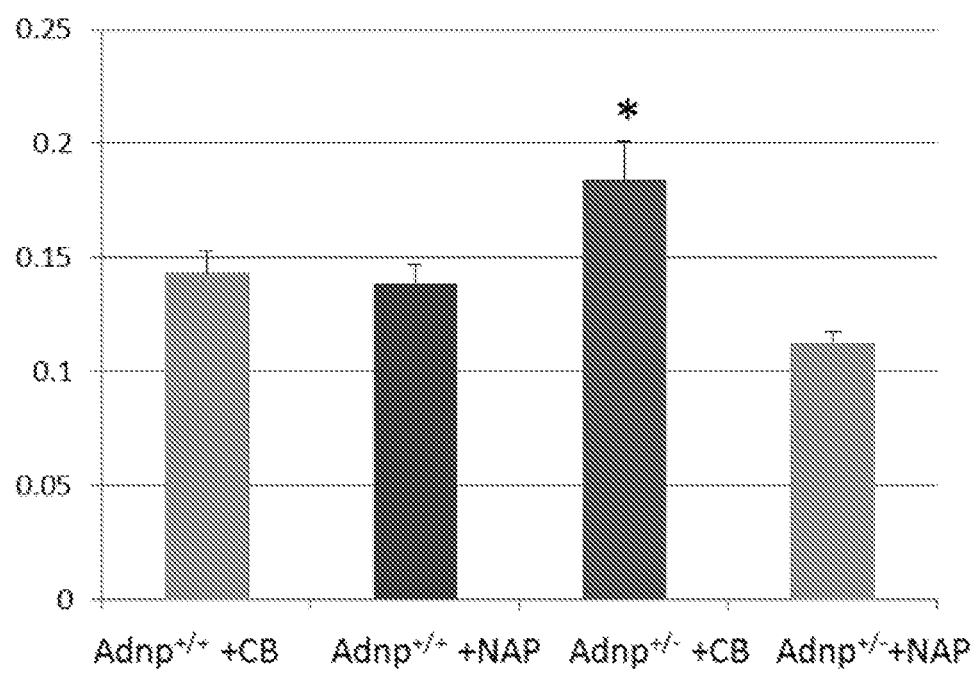

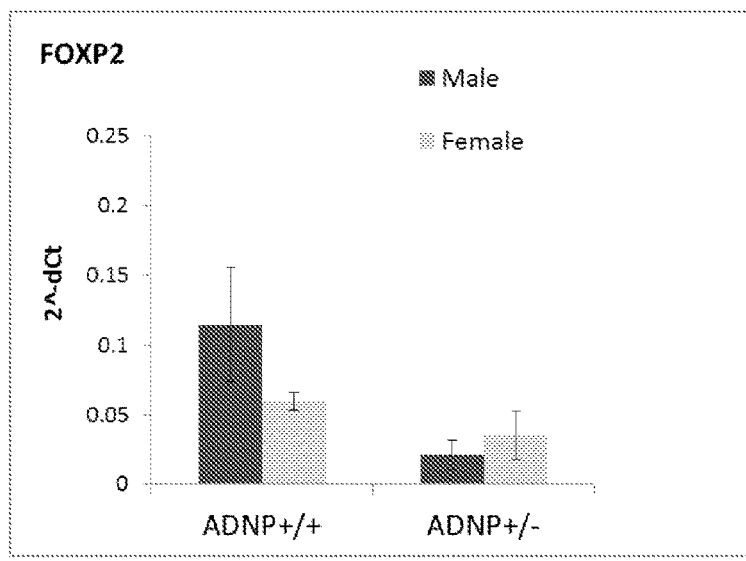
Fig. 8A
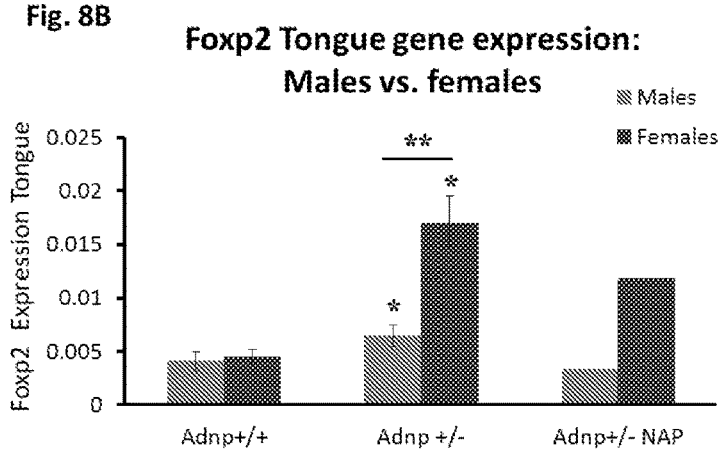
Fig. 8B
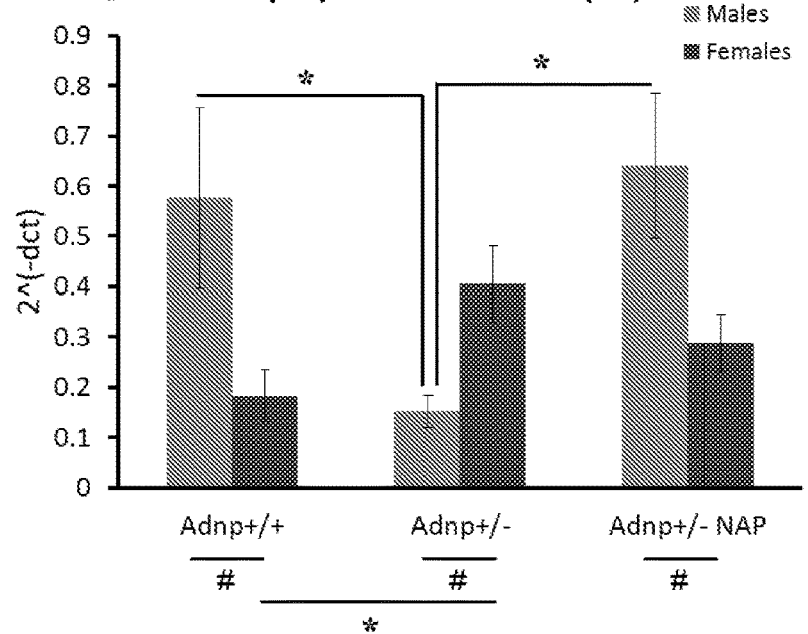

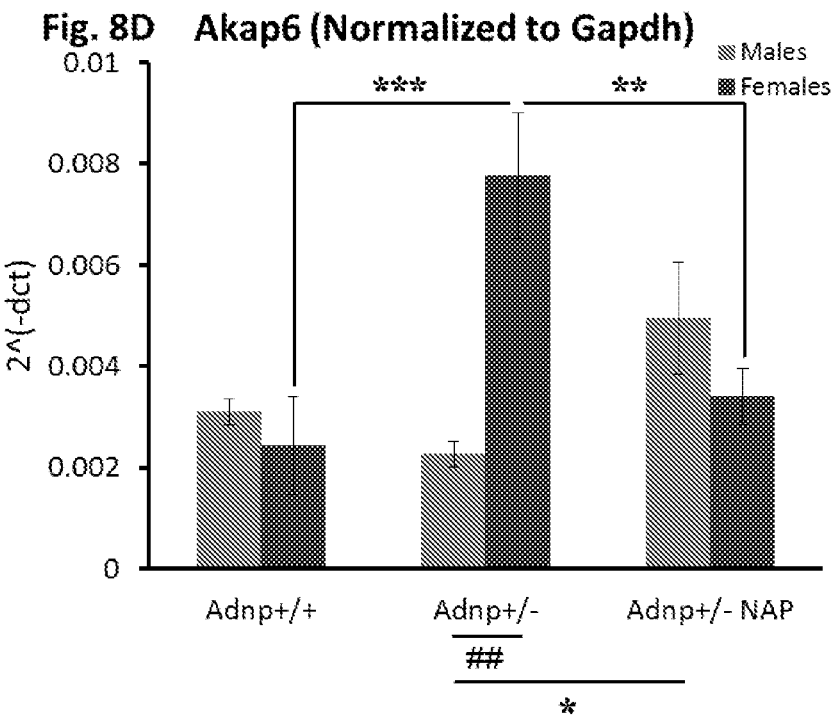
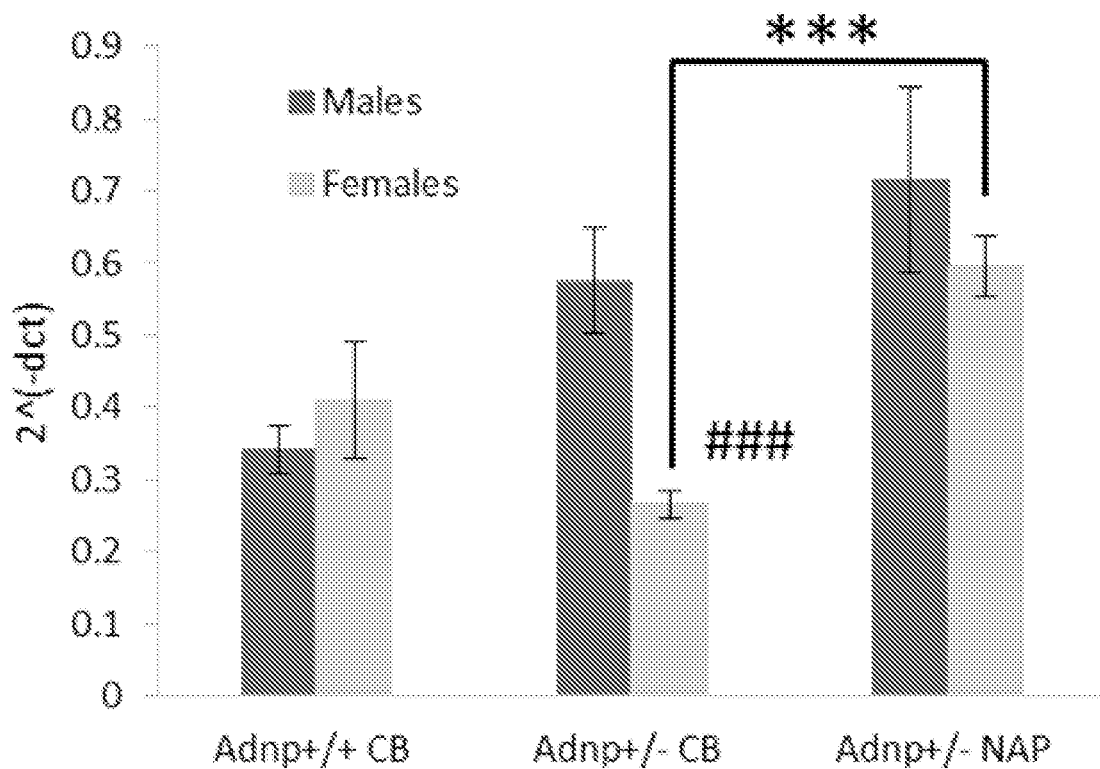

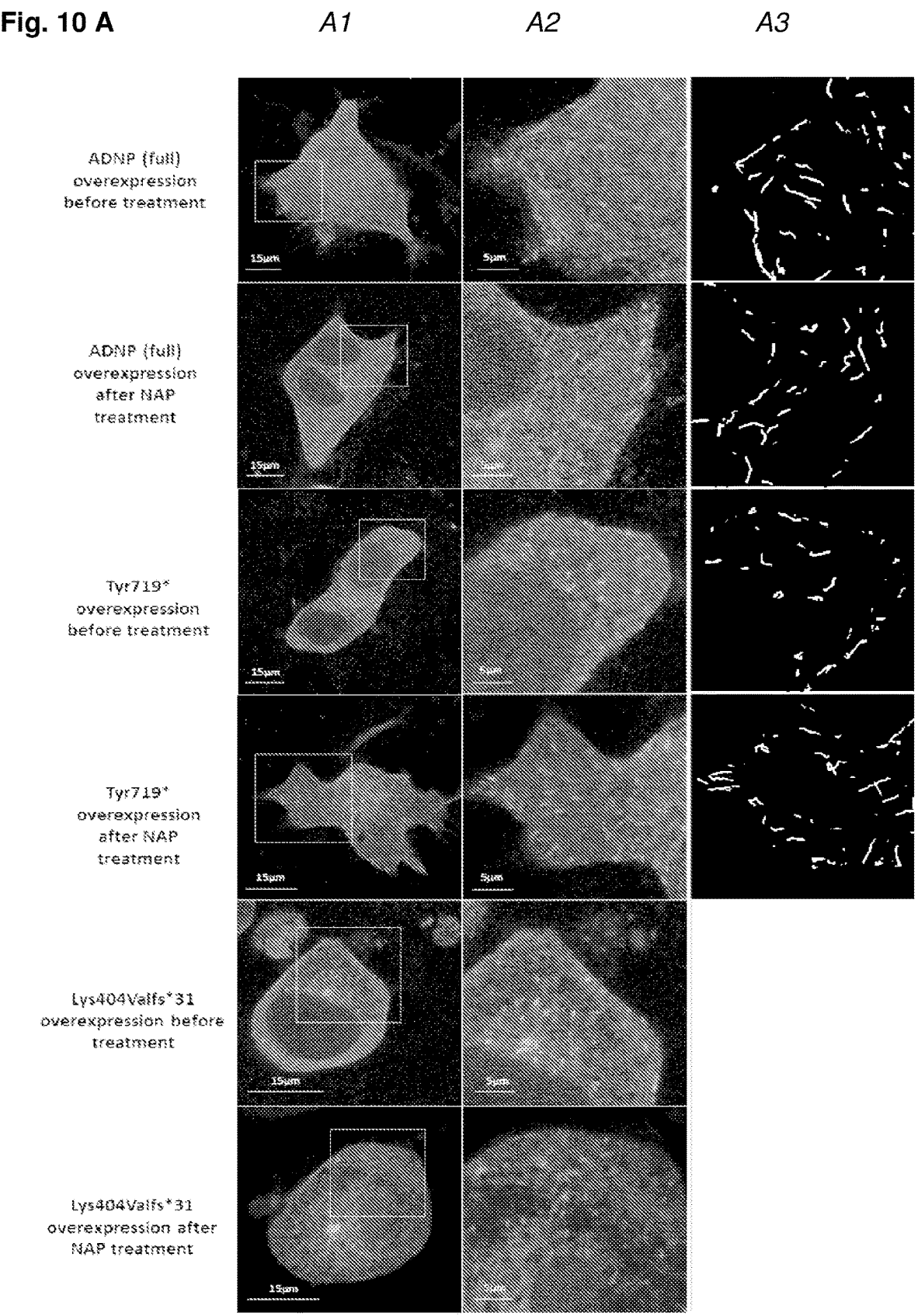

NEUROPROTECTIVE PEPTIDES DERIVED FROM ACTIVITY-DEPENDENT NEUROPROTECTIVE PROTEIN FOR TREATMENT OF NEUROLOGICAL DISEASES

RELATED APPLICATIONS

This application claims priority to U.S. Provisional Patent Application No. 62/288,239, filed Jan. 28, 2016, the contents of which are incorporated by reference in the entirety for all purposes.

SEQUENCE LISTING

The instant application contains a Sequence Listing which has been filed electronically in ASCII format and is hereby incorporated by reference in its entirety. Said ASCII copy, created on Jun. 2, 2020, is named 103410-1093840-001810US_SL.txt and is 1,872 bytes in size.

BACKGROUND

While chlorobutanol has been in use as a preservative in various pharmaceutical formulations including nasal sprays, it was previously not known nor understood that it has any notable effect on the absorption of a bioactive peptide drug. The present inventor surprisingly discovered that, aside from its preservative role, chlorobutanol can significantly enhance the bioavailability of a peptide drug, so that the peptide drug can be achieved in the targeted delivery site such as the brain at a greatly increased efficiency. On the other hand, neuroprotective peptides have shown promising effectiveness in the treatment of various neurodegenerative diseases and mental disorders including Alzheimer's disease, Parkinson's disease, schizophrenia, anxiety, depression, and autism including developmental retardation. Additionally, these neuroprotective peptides can provide protection against ocular diseases including but not limited to glaucoma and age-related macular degeneration. Furthermore, these peptide can protect against devastating outcomes of drugs of abuse, such as alcohol or cocaine.

Given the prevalence of neurodegenerative disorders, their serious implications, and the lack of effective treatment, there exists a pressing need for further research to find an effective therapy for these devastating conditions. The findings described herein offer a novel formulation for future therapeutic applications with enhanced efficacy.

BRIEF SUMMARY OF THE INVENTION

The present invention relates to novel formulations and methods for delivering to patients in need thereof peptides having desirable pharmaceutical activity, such as ADNP-related neuroprotective peptides, with enhanced bioavailability.

In a first aspect, this invention provides a novel composition or formulation of a peptide to be administered to a patient. The composition comprises a peptide of a desired bioactivity and chlorobutanol. In some embodiments, the peptide is a neuroprotective peptide derived from activity-dependent neuroprotective protein (ADNP), or an ADNP-related neuroprotective peptide, such as NAP or SKIP (SEQ ID NO:2).

In some embodiments, the concentration of chlorobutanol in the formulation is between about 0.05 to 5%, 0.1 to 1%, or 0.2 to 0.5% weight/weight. For example, the concentration of chlorobutanol is 0.25% in some cases. In some embodiments, the formulation further comprises 0.85% NaCl and has a pH of about 3.5 or about 4.0. In some embodiments, the concentration of the peptide is between about 1-250, 5-200, or 10-100 mg/ml. In some embodiments, the formulation is one formulated specifically for nasal administration, such as a nasal spray. In some embodiments, the formulation further includes an anti-psychotic agent, such as Aripiprazole, Clozapine, Ziprasidone, Resperidone, Quetiapine, or Olanzapine, for treatment of a mental disorder such as schizophrenia or a choline esterase inhibitor or mementine for treating dementia.

In a second aspect, this invention provides a method for effectively delivering a peptide having desirable pharmaceutical activity. The method is intended to deliver the composition or formulation described above to a patient in need thereof so as to provide an effective amount of the peptide, and it comprises the step of administering a composition or formulation containing the peptide in an effective amount and chlorobutanol. In some embodiments, the administering step comprises nasal administration of the formulation.

In some embodiments, the patient is an individual that is diagnosed of or at risk of developing schizophrenia, anxiety, depression, mania, cognitive/emotional disabilities associated with aging or mild cognitive impairment predicting Alzheimer's disease, Alzheimer's disease, frontotemporal dementia, Parkinson's disease and related disorders, diabetes and associated neuropathies, cancer therapy related neuropathies, multiple sclerosis, amyotrophic lateral sclerosis (ALS), Huntington disease and all related chronic degenerations, brain development associated disabilities, motor disabilities especially in those affected by ADNP-mutation including children and schizophrenic patients, autism spectrum disorders (ASDs), Down's syndrome and related chromosomal aberrations, fetal alcohol syndrome and cerebral palsy, juvenile and adult drug addiction, acute brain injury including but not limited to, head trauma and stroke, as well as ocular/ophthalmic injuries and chronic diseases such as glaucoma, age related macular degeneration etc. and inflammatory diseases such as ileitis, colitis, Crohn's disease and arthritis. In some embodiments, the composition comprises NAP or SKIP (SEQ ID NO; 2) at the concentration of about 1-250, 5-200, or 10-100 mg/ml, chlorobutanol at the concentration of about 0.05 to 5%, 0.1 to 1%, or 0.2 to 0.5% weight/weight (e.g., 0.25% w/w), 0.85% NaCl, and has a pH of about 3.5 or about 4.0. In some embodiments, the patient is an ADNP-mutated child or adult, i.e., a child or adult whose ADNP gene contains at least one genetic mutation in its coding or non-coding sequence so as to affect the expression and/or activity of ADNP. In some embodiments, the composition is administered once or twice every day. For each administration, a patient is given the peptide in the amount of 1-2000, 2-1000, 6-600, 20-100, or 16-70 µg/kg body weight. In some embodiments, the composition is administered for a time period of 1 week, 10 days, 2 weeks, 1 month, 6 months, 1 year, or for a much longer period such as 2, 5, 7, 10, 15, 20 years or for the duration of patient's life. The term "about" when used in this disclosure in reference to a given value denotes a range of +/−10% of that value. In some embodiments, the peptide is administered to the patient in a differential manner based on gender: for a male patient, e.g., a man or boy, a relatively lower amount of the peptide is administered (i.e., a lower effective amount is needed), whereas when the patient is female, e.g., a woman or girl, a relatively higher amount of the peptide is administered (i.e., a higher effective amount is needed).

In a related aspect, the present invention provides a method for delivering to a patient a neuroprotective peptide derived from ADNP or regulating ADNP, especially when the patient has weak arms and diminished muscle strength and is therefore in need of improvement of muscle strength. The method comprises administering to the patient a composition comprising an effective amount of the peptide (such as NAP or SKIP (SEQ ID NO:2) or ADNP regulating peptides/agents) and benzalkonium chloride.

BRIEF DESCRIPTION OF THE DRAWINGS

FIG. 1. The presence of chlorobutanol in the formulation results in brain concentration, homogeneous brain distribution. A. Experiments were performed as described in the method section. The upper panel shows the picture of two mice and the lower panel shows the Maestro results, after the application of labeled NAP. B. The upper panel shows the picture of two mouse brains and the lower panel shows the Maestro results, after the application of labeled NAP, decapitation and brain removal. C. The Maestro results, after the application of labeled NAP, decapitation and brain removal were calculated. It should be added here that chlorobutanol is usually used for topical formulations and this can also be implemented. Surprisingly here, there seems to be no difference between the formulations.

Figure 2A:
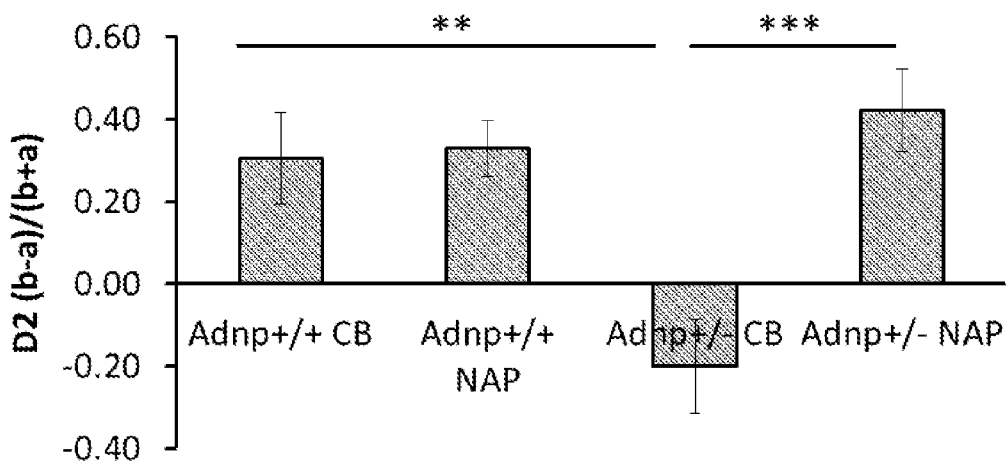
FIG. 2. NAP treatment increases the relative discrimination between novel and familiar objects. Animal performance in the object recognition test is shown. A,B, n=9-12 male mice per group, age 6-9 months, treated with NAP-CB or CB alone, CB=0.25% Chlorobutanol, 0.85% NaCl, pH 3.5 (pH can be adjusted to 4.0).

Data are expressed as mean (±SEM) total time (sec) spent exploring all objects designated by relative discrimination index (a and b-exploration of familiar and novel object, respectively) in Phase 2 (A) and Phase 3 (B). Two identical objects were presented during Phase 1 (habituation), and one of the identical objects was replaced by a novel object during Phases 2 and 3. Adnp-deficient mice spent significantly less time in exploring the new objects during Phases 2 (A, 3 hours after habituation) and 3 (B, 24 hours after habituation), as compared to control mice (Adnp$^{+/+}$). For short retention choice phase, two-way ANOVA revealed significant treatment (F(1,38)=9.66, p=0.004) and interaction (F(1,38)=8.231 p=0.007) effects. Significant differences were found with Fisher's LSD post hoc test between Adnp$^{+/+}$ and Adnp$^{+/-}$ mice (p<0.01), and between Adnp$^{+/-}$ and NAP-treated Adnp$^{+/-}$ mice (*p<0.001). For long retention choice phase, two-way ANOVA revealed significant genotype (F(1,38)=10.813, p=0.002), treatment (F(1,38)=4.584, p=0.039) and interaction (F(1,38)=16.940, p<0.001) effects. Significant differences were found with Fisher's LSD post hoc test between Adnp$^{+/+}$ and Adnp$^{+/-}$ mice (*p<0.001), and between Adnp$^{+/-}$ and NAP-treated Adnp$^{+/-}$ mice (*p<0.001). (C) 2-month-old mice (n=3-4 males or 6-8 females per experimental group) were treated daily, five times a week for 6 weeks with 0.5 µg NAP/mouse/day by intranasal administration in DD=7.5 mg/ml of NaCl, 1.7 mg/ml of citric acid monohydrate, 3 mg/ml of disodium phosphate dihydrate, and 0.2 mg/ml of 50% benzalkonium chloride solution. Animal performance in the object recognition test after four week treatment is shown. Data are expressed as mean (±SEM) as above, in the long retention choice phase (24 hours after habituation). This is in comparison to Malishkevich et al., *Transl Psychiatry* (2015) 5, e501, who showed that at 7-9 months of age, Adnp+/- males were impaired, while female mice showed only a trend. Here, in younger mice, Adnp-deficient females spent significantly less time in exploring the new objects during the long retention phase, as compared to control mice (Adnp+/+) with NAP normalizing the deficient female behavior. Two-way ANOVA revealed a significant main genotype effect (F(1,26)=4.669, p=0.041). Significant differences were found with Fisher's LSD post hoc test between Adnp+/+ and Adnp+/- mice (*p<0.05), and between Adnp+/- and NAP-treated Adnp+/- mice (*p<0.05). Males showed only a trend—possibly due to the small group size. No differences were observed in the short retention phase as was seen with the same vehicle in older mice (Malishkevich et al., *Transl Psychiatry* (2015) 5, e501). However, differences were seen in the short retention phase with NAP-CB (FIG. 2A) suggesting a vehicle-dependent effect.

FIG. 3. NAP treatment increases social memory. Animal performance is shown. (A, animals were as in FIG. 2A,B; n=9-12 per group). Data are expressed as mean±SEM total time (sec) spent exploring mice designated by relative discrimination index (D2=(b-a)/(a+b); b=time sniffing novel mouse, a=time sniffing familiar mouse). An empty wire cup and a cup containing target mouse ("familiar") were placed in the center of the right or left chamber. After 3 hours, a novel mouse was put inside the empty cup, while the other cup contained the familiar mouse. The Adnp$^{+/-}$ mice spent less time in exploring the novel mouse, as compared to Adnp$^{+/+}$ mice. Treatment with NAP improved social memory for the Adnp$^{+/-}$ mice. Two-way ANOVA revealed main effects for genotype (F(1,34)=18.698, p<0.001), treatment (F(1,34)=43.431, p<0.001) and interaction (F(1,34)=23.066, p<0.001). Fisher's LSD post hoc test revealed a significant difference between Adnp$^{-/+}$ and Adnp$^{+/-}$ mice under vehicle treatment (*p<0.001). In addition, there was a significant difference between vehicle and NAP treatments in the Adnp$^{+/-}$ mice (*p<0.001).

Two additional confirmatory experiments were performed as follows: (B) 5-month-old mice (n=4 per experimental group) were treated daily, five times a week for 8 weeks with 0.5 µg NAP/mouse/day by intranasal administration in CB. as in FIG. 2.

Adnp$^{+/-}$ mice spent significantly less time in exploring the novel mouse, as compared to their controls. Treatment with NAP improved social memory for Adnp$^{+/-}$ mice. For males, two-way ANOVA revealed main effects for treatment (F(1,10)=6.402, p=0.035) and genotype (F(1,10)=5.443, p=0.048). Fisher's LSD post hoc test revealed a significant difference between NAP- and vehicle-treated Adnp$^{+/-}$ mice (*p<0.05). In addition, there was a significant difference between Adnp$^{+/+}$ and Adnp$^{+/-}$ mice (*p<0.05). For females, two-way ANOVA revealed main effects for treatment (F(1,10)=10.984, p=0.011) and genotype (F(1,10)=6.046, p=0.039). Fisher's LSD post hoc test revealed a significant difference between NAP- and vehicle-treated Adnp$^{+/-}$ mice (*p<0.05). In addition, there was a significant difference between vehicle-treated Adnp$^{+/+}$ and Adnp$^{+/-}$ mice (*p<0.05).

Figure 2B:
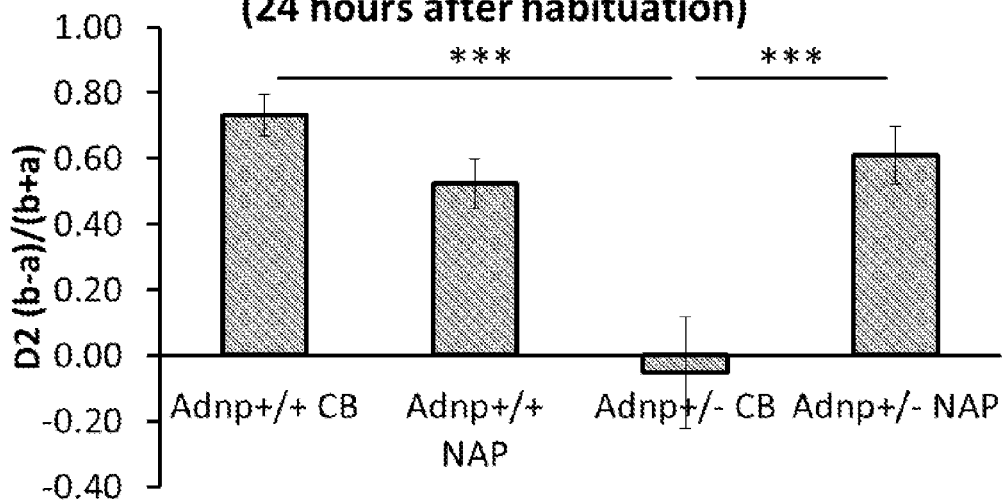

(C) 2-month-old mice (n=3-4 males or 6-8 females per experimental group) were treated daily, five times a week for 7 weeks with 0.5 µg NAP/mouse/day by intranasal administration in DD, as above, FIG. 2.

For males, two-way ANOVA revealed main effect for genotype (F(1,14)=6.195, p=0.030). Fisher's LSD post hoc test revealed a significant difference vehicle-treated Adnp$^{+/+}$ and Adnp$^{+/-}$ mice (*p<0.05). For females, two-way ANOVA revealed main effect for treatment (F(1,19)=5.021, p=0.039). Fisher's LSD post hoc test revealed a significant difference between NAP- and vehicle-treated Adnp+/− mice (*p<0.05).

As social memory depends on olfactory function, NAP treatment was also tested in odor discrimination test. Odors were presented on a suspended cotton swab to the test mouse placed into the clean cage with fresh shavings. Each mouse was tested during three consecutive 2-min periods for each odor, with 2-min intervals between presentations. The x axis indicates the consecutive number of the odor exposure period. The time that the mouse smelled the swab was recorded (beginning whenever the animal oriented its nostrils toward the cotton swab, within 2 cm or less). (Malishkevich et al., *Transl Psychiatry* (2015) 5, e501; Amram et al., *Mol Psychiatry.* 2016 10:1467-76).

Females:

(D) 5-month-old mice (n=4 per experimental group) were treated daily, five times a week for 9 weeks with 0.5 μg NAP/mouse/day by intranasal administration in CB.

No significant changes were observed vs. previous sniffing (novel vs. familiar odor), paired t-test. For each experimental group, general olfaction ability was measured by calculating area under the curve (AUC)-inset graph. Two-way ANOVA revealed main effects for genotype (F(1,9)=5.947, p=0.045) and treatment (F(1,9)=13.794, p=0.008). Fisher's LSD post hoc test revealed a significant difference between vehicle-treated $Adnp^{+/+}$ and $Adnp^{+/-}$ mice (*p<0.05), as well as NAP- and vehicle-treated $Adnp^{+/-}$ mice (**p<0.01).

(E) 2-month-old mice (n=6-8 males per experimental group) were treated daily, five times a week for 8 weeks with 0.5 μg NAP/mouse/day by intranasal administration in DD. *p<0.05 vs. previous sniffing (novel vs. familiar odor), paired t-test. For each experimental group, general olfaction ability was measured by calculating area under the curve (AUC)-inset graph. Two-way ANOVA revealed main effect for treatment (F(1,20)=5.138, p=0.036). Fisher's LSD post hoc test revealed a significant difference between NAP- and vehicle-treated $Adnp^{+/-}$ mice (*p<0.05).

Males:

(F) 5-month-old mice (n=4 per experimental group) were treated daily, five times a week for 9 weeks with 0.5 μg NAP/mouse/day by intranasal administration in CB. *p<0.05, p<0.01, *p<0.001 vs. previous sniffing (novel vs. familiar odor), paired t-test. For each experimental group, general olfaction ability was measured by calculating area under the curve (AUC)-inset graph. Two-way ANOVA revealed main effect for treatment (F(1,11)=5.563, p=0.043). Fisher's LSD post hoc test revealed a significant difference between NAP- and vehicle-treated $Adnp^{+/-}$ mice (*p<0.05).

(G) 2-month-old mice (n=3-4 males per experimental group) were treated daily, five times a week for 8 weeks with 0.5 μg NAP/mouse/day by intranasal administration in DD. *p<0.05 vs. previous sniffing (novel vs. familiar odor), paired t-test. For each experimental group, general olfaction ability was measured by calculating area under the curve (AUC)-inset graph. Two-way ANOVA revealed main effect for treatment (F(1,10)=5.586, p=0.046).

Figure 4:
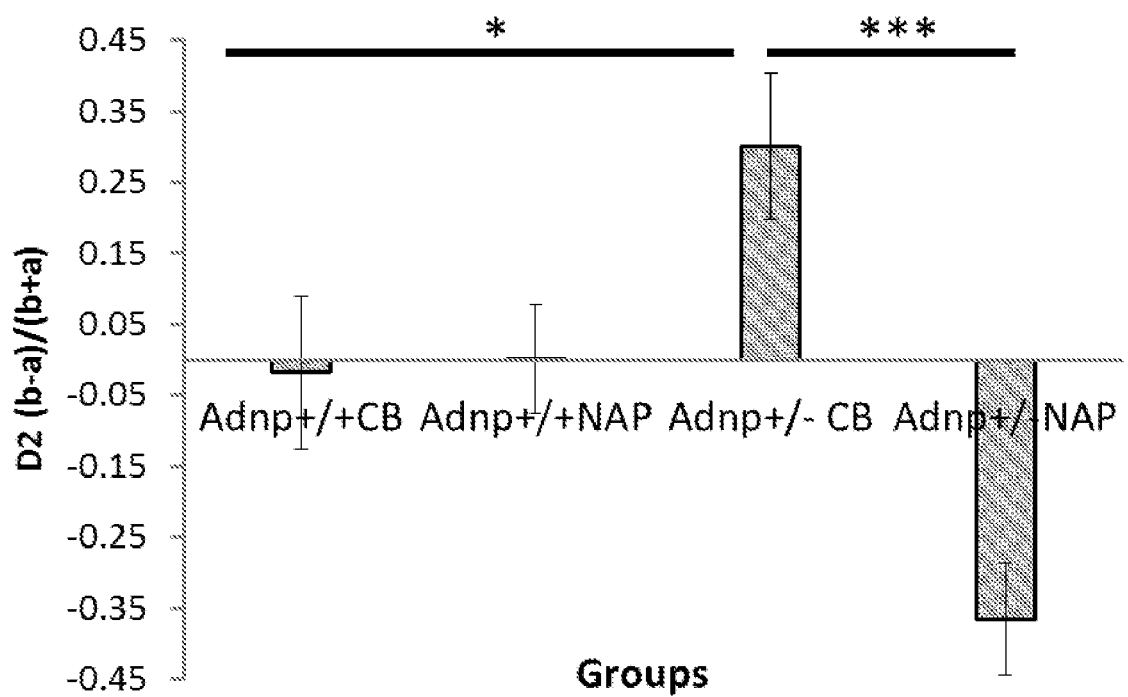

FIG. 4. $Adnp^{+/-}$ male mice exhibit increased anxiety in the elevated plus maze test, ameliorated by NAP treatment. The relative time spent in the open/closed arms for 5 min is presented (n=9-12 per group). Data are expressed as mean±SEM. D2 calculates the exploration time of the open arms (a) and the exploration time of the closed arms (b). $Adnp^{+/-}$ mice spent significantly more time in the closed arms compared to $Adnp^{+/+}$ mice. Two-way ANOVA revealed significant main effects for treatment (F(1,39)=11.233, p=0.002) and interaction (F(1,39)=12.668, p=0.001). A significant difference was found with Fisher's LSD post hoc test in the time spent in the open/closed arms between $Adnp^{+/+}$ mice and $Adnp^{+/-}$ mice (*p<0.05). A significant difference was also found between $Adnp^{+/-}$ and NAP-treated $Adnp^{+/-}$ mice (***p<0.001).

FIG. 5. NAP-treated $Adnp^{+/+}$ and $Adnp^{+/-}$ male mice exhibit decreased anxiety in an open field apparatus. Furthermore, NAP ameliorates motor dysfunction in $Adnp^{+/-}$ mice. Each male mouse (n=9-12 per group) was placed in the middle of the field and allowed to freely explore the arena for 15 min. The duration in center zone (A), and the total path traveled (B) were measured by the Ethovision XT video tracking system (Noldus Inc. Leesburg, Va.). Two-way ANOVA revealed a significant main treatment effect for the duration in center zone (sec) (F(1,40)=4.837 p=0.034, A). A significant difference was found with Fisher's LSD post hoc test between NAP-treated and vehicle-treated mice of both genotypes (*p<0.05). For total path traveled, two-way ANOVA revealed main genotype effect (F(1, 40)=6.900, p=0.012, B). A significant difference was found with Fisher's LSD post hoc between vehicle-treated $Adnp^{+/+}$ and $Adnp^{+/-}$ (*p<0.05).

C, D) Hanging Wire Test: $Adnp^{+/-}$ mice display decreased latency to fall in age- and sex-dependent manner—NAP protects The hanging wire test measures the strength of the mouse paws by using the latency to fall off from an inverted cage lid (placed 50 cm above the surface) onto a soft bedding (maximum time 120 sec). Data are expressed as mean±SEM.

(C) 2-month-old mice (n=3-4 males or 6-8 females per experimental group) were treated daily, five times a week for 5 weeks with 0.5 μg NAP/mouse/day by intranasal administration in DD.

Male $Adnp^{+/-}$ mice exhibited decreased latency to fall, as compared to $Adnp^{+/+}$ mice, which was improved by NAP treatment. For male mice, two-way ANOVA revealed significant main effect for interaction (F(1,13)=9.589, p=0.011). A significant difference was found with Fisher's LSD post hoc test between $Adnp^{+/+}$ mice and $Adnp^{+/-}$ mice (p<0.01), as well as $Adnp^{+/-}$ and NAP-treated $Adnp^{+/-}$ mice (p<0.01). Sexual dichotomy was also observed in $Adnp^{+/-}$ mice (#p<0.05).

(D) 5-month-old mice (n=4 per experimental group) were treated daily, five times a week for 3 weeks with 0.5 μg NAP/mouse/day by intranasal administration in CB.

For males, two-way ANOVA revealed significant main effects for genotype (F(1,11)=19.958, p=0.002) and treatment (F(1,11)=5.442, p=0.045). A significant difference was found with Fisher's LSD post hoc test between $Adnp^{+/+}$ mice and $Adnp^{+/-}$ mice (**p<0.01). A significant difference was also found between $Adnp^{+/-}$ and NAP-treated $Adnp^{+/-}$ mice (*p<0.05). For 5-month-old female mice, two-way ANOVA revealed significant main effects for genotype (F(1, 10)=34.320, p<0.001) and treatment (F(1,10)=6.449, p=0.035). A significant difference was found with Fisher's LSD post hoc test between $Adnp^{+/+}$ mice and $Adnp^{+/-}$ mice (***p<0.001). A significant difference was also found between $Adnp^{+/-}$ and NAP-treated $Adnp^{+/-}$ mice (*p<0.05).

Grip Strength Test: $Adnp^{+/-}$ mice exhibit significant decreased grip force—NAP protects The grip strength test measures forelimbs muscle strength using the UgoBasile 47200-Grip-Strength Meter. Each animal was tested five times and the peak force of each mouse was recorded. Data are expressed as mean±SEM.

(E) 2-month-old mice (n=3-4 males or 6-8 females per experimental group) were treated daily, five times a week for 5 weeks with 0.5 µg NAP/mouse/day by intranasal administration in DD.

Adnp$^{+/-}$ male mice exhibited reduced muscle strength, as compared to Adnp$^{+/+}$ mice, with NAP significantly improving it. For male mice, two-way ANOVA revealed significant main effects for genotype ($F(1,13)=9.358$, $p=0.012$) and interaction ($F(1,13)=9.030$, $p=0.013$). A significant difference was found with Fisher's LSD post hoc test between vehicle-treated Adnp$^{+/+}$ and Adnp$^{+/-}$ mice (**$p<0.01$), as well as between vehicle- and NAP-treated Adnp$^{+/-}$ mice (*$p<0.05$).

(F) 5-month-old mice (n=4 per experimental group) were treated daily, five times a week for 4 weeks with 0.5 µg NAP/mouse/day by intranasal administration in CB. Adnp$^{+/-}$ female mice exhibited reduced muscle strength, as compared to Adnp$^{+/+}$ mice. For female mice, two-way ANOVA revealed significant main effects for genotype ($F(1,11)=8.226$, $p=0.018$). A significant difference was found with Fisher's LSD post hoc test between vehicle-treated Adnp$^{+/+}$ and Adnp$^{+/-}$ mice (*$p<0.05$). Sexual dichotomy was also observed between Adnp$^{+/-}$ males and females (#$p<0.05$).

FIG. 6: NAP protects against increases in hippocampal mean diffusivity (MD) and fractional anisotropy (FA) in the Adnp$^{+/-}$ mice. (A) In the hippocampal area located -1.84 mm from Bregma, a significant increased mean diffusivity (MD) was found in chlorobutanol (CB)-treated Adnp$^{+/-}$ mice, as compared to their Adnp$^{+/+}$ counterparts (* $p<0.05$). This increase, although insignificantly, was reduced in NAP-treated Adnp$^{+/-}$ mice.

(B) In the hippocampal area located -2.34 mm from Bregma, a significant increased fractional anisotropy (FA) was found in chlorobutanol (CB)-treated Adnp$^{+/-}$ mice, as compared to their Adnp$^{+/+}$ counterparts (* $p<0.05$). This increase was significantly reduced in NAP-treated Adnp mice (* $p<0.05$).

Figure 7:
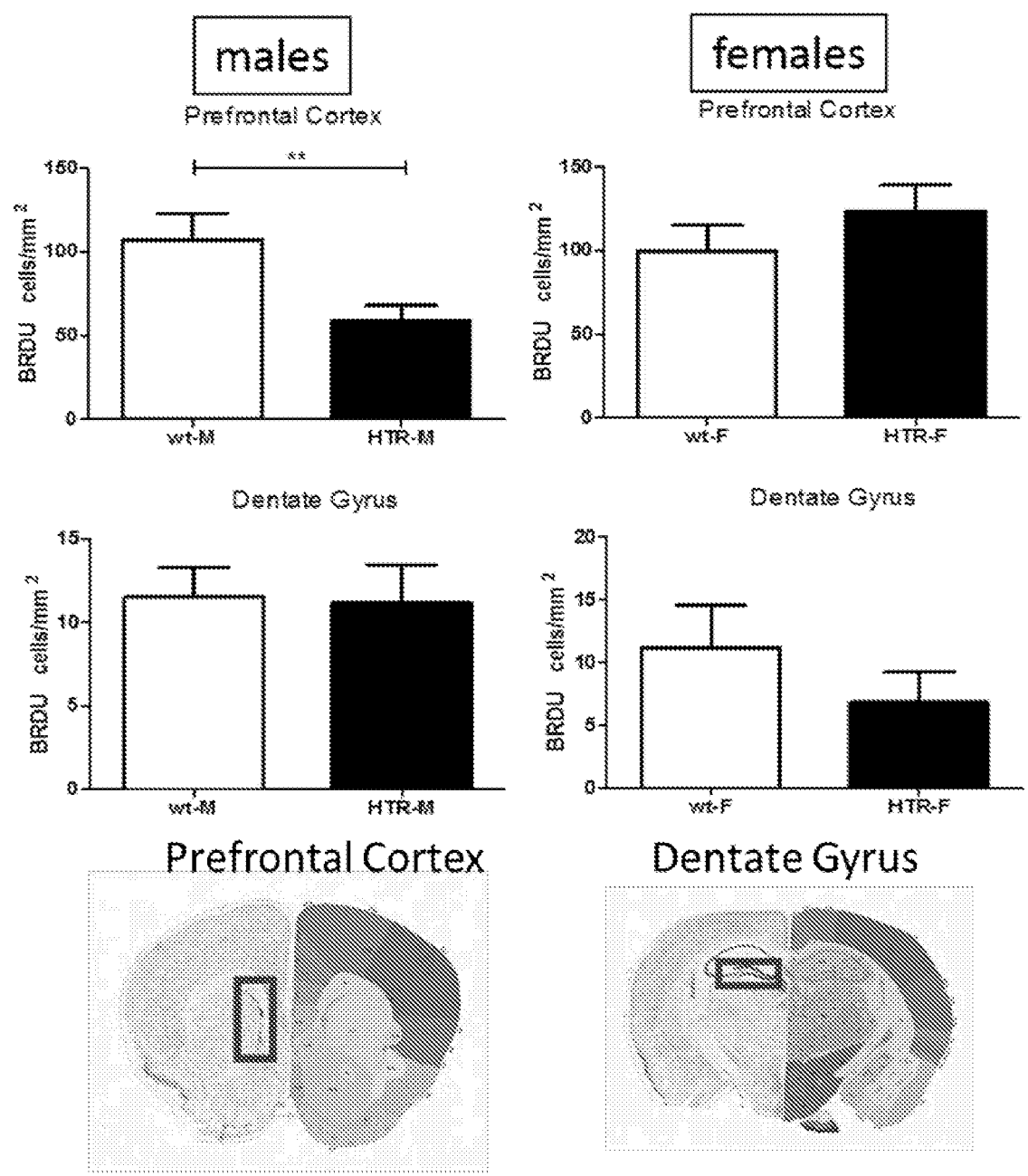

FIG. 7: Adnp deficiency is associated with reduced stem cell proliferation. One month old Adnp mice (Adnp$^{+/+}$ (wt) and Adnp$^{+/-}$ (HTR), male and female, n=5) were injected with 80 mg/kg BRDU, diluted in PBS, every 2 hours (4 doses) and sacrificed within one hour after the last injection. BRDU stained cells were counted (cells/mm$^2$) in the dentate gyrus and prefrontal cortex. Adnp male mice show significantly less BRDU staining in prefrontal cortex, compared to Adnp$^{+/+}$ ($p<0.005$). In contrast, Adnp$^{+/-}$ females show only a reduction trend in the dentate gyrus ($p>0.05$). Thus, it seems that Adnp levels have a potential effect on the proliferation process of brain stem cells which differs according to gender and brain location. Experiments were performed together with the laboratory of Professor Grigoriadis in Greece.

FIG. 8: Adnp deficiency is associated with deregulated Foxp2 expression. 6-month-old-mice with Adnp—deficiency showed altered Foxp2 expression (for experimental details see—(Malishkevich, A., et al., Transl Psychiatry 5:e501.). Results are shown for hippocampal gene expression (A).

(B) Foxp2 (the language-linked gene) expression in the tongue is increased in Adnp-deficient mice and is normalized by NAP. Tongue total RNA was extracted from 4-month-old mice (treated with NAP/DD as above) and analyzed for Foxp2 and Gapdh mRNA expression by quantitative real-time PCR (n=3-7 animals per experimental group). Gapdh served as a normalizing transcript. Foxp2 showed a significantly increased expression in both Adnp' males and females, with NAP normalizing it in males and decreasing it in females (*$p<0.05$). Two-way ANOVA analysis was performed using SigmaPlot. Sexual dichotomy determined by t-test analysis was also observed for the increased Foxp2 expression between Adnp males and females (**$p<0.01$).

(C) Recently discoveries show altered gene regulation in association with Adnp deficiency and ADNP mutations (Amram N. et al., Mol Psychiatry. 201621:1467-76; Gozes I. J Neurosci Res. 2017; 95:652-660. Gozes I. et al., Translational Psychiatry, under review). One of the major genes that was changed in terms of expression is the A-kinase anchor protein, AKAP6.

Here, NAP regulates Akap6 tongue gene expression in a sex-dependent manner:

Tongue total RNA was extracted from 4-month-old mice (treated with NAP/DD as above) and analyzed for Akap6, Hprt, and Gapdh mRNA expression by quantitative real-time PCR (n=6-14 replicates per experimental group). HPRT and Gapdh served as normalizing transcripts.

(C) Akap6 normalized to Hprt: Adnp$^{+/-}$ male mice exhibited a significantly decreased Akap6 expression, compared to Adnp$^{+/+}$ and NAP-treated Adnp$^{+/-}$ mice (*$p<0.05$). Adnp$^{+/-}$ female mice exhibited a significantly increased expression, compared to Adnp$^{+/+}$ mice (*$p<0.05$).

(D) Akap6 normalized to Gapdh: NAP-treated Adnp$^{+/-}$ male mice displayed a significantly increased AKAP6 expression, compared to vehicle-treated Adnp$^{+/-}$ mice (*$p<0.05$). Adnp$^{+/-}$ female mice displayed a significantly increased expression, compared to Adnp$^{+/+}$ and NAP-treated Adnp$^{+/-}$ mice ($p<0.01$, *$p<0.001$).

Two-way ANOVA analysis with Fisher's LSD as post hoc was performed using SigmaPlot. Sexual dichotomy determined by t-test analysis was also observed for Adnp$^{+/+}$, Adnp'$^{+/-}$ and NAP-treated Adnp$^{+/-}$ mice when normalizing Akap6 to Hprt (#$p<0.05$), and only in Adnp$^{+/-}$ mice when normalizing Akap6 to Gapdh (##$p<0.01$).

In females, NAP regulates genes deregulated with ADNP mutation in the hippocampus. Hippocampal total RNA was extracted from 7.5-month-old mice (treated with NAP/CB as above) and analyzed for Akap6 (E), Cell Adhesion Molecule L1 Like (Chip (F), and Hprt (standard) mRNA expression by quantitative real-time PCR (n=6-12 replicates per experimental group). Hprt served as a normalizing transcript. In males, Chl1 showed a significantly increased expression in vehicle-treated Adnp$^{+/-}$ mice, compared to their Adnp$^{+/+}$ counterparts (**$p<0.01$). In females, Akap6 showed a significantly increased expression in NAP-treated Adnp$^{+/-}$ mice, compared to vehicle-treated Adnp$^{+/-}$ mice. Two-way ANOVA analysis with Fisher's LSD as post hoc was performed using SigmaPlot. Sexual dichotomy determined by t-test analysis was also observed for Akap6 and Chl1 expression between Adnp$^{+/-}$ males and females (#$p<0.05$, ##$p<0.01$, ###$p<0.001$).

FIG. 9: NAP treatment protected against vocalization deficiency in Adnp$^{+/-}$ mice. Furthermore, Auditory brain response (ABR) of 2.5 months old mice presents prolonged latency of hearing in Adnp+/- vs. Adnp+/+ females. (A) Results are presented as means±SEM. Ultrasonic vocalizations (USVs) were recorded in eight-day-old pups, subjected to daily subcutaneous injections of NAP (25 µg/ml saline) or saline (20 µl and 40 µl on postnatal days 1-4 and 5-7). The recordings were performed following dam separation according to published literature (Shu, W., et al. 2005. Proc Nati Acad Sci USA 102:9643-9648) NAP was injected as described before (Rotstein, M., et al., 2006. J Pharmacol Exp Ther 319:332-339). A two way analysis of variance (ANOVA) comparison of the average number of USVs produced in a minute revealed statistically significant treatment effect (p=0.029) and a genotype-treatment interaction (p=0.011). All Pairwise Multiple Comparison Procedures (Fisher LSD Method) revealed a significant increase in the number of USVs produced by Adnp$^{+/-}$ treated with NAP compared to Adnp control group (**p=0.005). In contrast, no significant treatment effect was found in Adnp$^{+/+}$ groups (p=0.73). A genotype effect was found between saline groups, as Adnp exhibit a significant reduction in USVs compared to littermates (*p=0.016).

(B,C) Adnp haploinsufficiency significantly reduces vocalization in mice, while NAP treatment reversed the phenotype (increasing the group size). (B) Adnp$^{+/-}$ pups were found to produce significantly less USV per minute, compared to Adnp$^{+/+}$ in females, with visible tendency in males. NAP administration increased vocalization in both sexes, compared to Adnp saline treated littermates, with most profound effect in males compared to females (#p<0.05, Student t test). (C) Similar results were obtained when the male and the female groups were combined, displaying significant reduction in USV and a most significant increase in USV following NAP daily injections (*p<0.05;p<0.005;*p<0.001). These results represent the potential in Adnp-language studies. Two-way ANOVA analysis was performed using Sigmaplot.

(D) Auditory brain response (ABR) of 2.5 months old mice presents prolonged latency of hearing in Adnp+/− vs. Adnp+/+ females. Hearing latency (sec) was evaluated by auditory brainstem responses (ABRs), recorded in response to tone bursts (kHz) in 2.5 months old mice (Walsh et al., *Mamm Genome* 22, 170-177 (2011); McCullough et al., *Hearing Research* 195, 90-102 (2004)). Auditory thresholds were determined by delivering pure tone auditory stimuli (tone bursts) binaurally at 5.6, 8, 11.3, 16, 32, and 40 kHz. Tone burst stimuli of alternating polarity were repeated at 75-ms intervals in 10-dB increments starting at 90 dB and decreasing to 20 dB. ABRs were recorded over 40 msec and averaged at each intensity level for 1024 presentations. Student's t-test comparison between Adnp+/−(HTR) (n=2) and Adnp+/+(WT) (n=2) female littermates at each tone (kHz) revealed a statistically significant difference (*p≤0.05).

FIG. 10: NAP ameliorates cytoskeletal deficiencies associated with ADNP mutations. Human ADNP mutated cDNA was cloned into plasmids as described (Ivashko-Pachima et al., *Molecular Psychiatry* 2017, in press). The mutations cloned included the p.Tyr719* ADNP, the most common ADNP mutation (Gozes et al., *Frontiers in Endocrinology*, under revisions) and the p.Lys408Valfs31*, the first de novo ADNP mutation identified (reviewed in Gozes et al., *J Mol Neurosci* (2015) 56:751-757.

The effects of ADNP carried p.Tyr719*/p.Lys404Valfs*31 mutation on microtubule end binding protein 1 and 3 (EB1 and EB3) comets in living N1E-115 is shown. For experimental details see, Ivashko-Pachima et al., *Molecular Psychiatry* 2017, in press. (A) Live imaging of N1E-115 cells. EB1-RFP (red) co-transfected with full ADNP/p.Tyr719*/p.Lys404Valfs*31 carrying plasmids before and after 4 hours NAP treatment ($10^{-12}$M) (panel A1). Time-lapse images were automatically captured every 3 sec during a 2 min period using the Leica LAS AF software. Details are presented in insets (panel A2). The figures of total tracks were performed with IMARIS software and tracks are presented as colored lines (panel A3). (B-C) EB1 Quantification of average track length, comet speed, comet length and number of comets/100 µm$^2$ (total number of comets: ADNP (full) before treatment n=2639/1 I cells, ADNP (full) after NAP treatment n=3107/15cells, ADNP p.Tyr719* before treatment n=1910/14cells, ADNP p.Tyr719* after NAP treatment n=3990/16cells, ADNP p.Lys404Valfs*31 before treatment n=1082/6cells, ADNP p.Lys404Valfs*31 after NAP treatment n=694/5cells). Data were collected by Imaris software, and statistical analysis of the data was performed by using One-way ANOVA by IBM SPSS Statistics software version 23 (*P<0.05,  P<0.01, * P<0.001). (D-G, EB3).

DETAILED DESCRIPTION OF THE INVENTION

Activity-Dependent Neuroprotective Proteins (ADNP) and ADNP-Related Neuroprotective Peptides ADNP-related neuroprotective peptides are peptides derived from activity dependent neurotrophic factors (ADNF) that have an active core site comprising the amino acid sequence of NAPVSIPQ (SEQ ID NO:1) (referred to as "NAP") or SALLRSIPA (SEQ ID NO:3) (referred to as "SAL"), or conservatively modified variants (e.g., deletion, addition, or substitutions of one or more amino acids) or chemically modified variants thereof, that have neurotrophic/neuroprotective activity as measured with in vitro cortical neuron culture assays described by, e.g., Hill et al., *Brain Res.* 603:222-233 (1993); Brenneman & Gozes, *J. Clin. Invest.* 97:2299-2307 (1996), Forsythe & Westbrook, *J. Physiol. Lond.* 396:515 (1988). An ADNF polypeptide can be derived from an ADNF I polypeptide, an ADNF III polypeptide, their alleles, polymorphic variants, analogs, interspecies homolog, any subsequences thereof (e.g., SALLRSIPA (SEQ ID NO:3) or NAPVSIPQ (SEQ ID NO:1)) or lipophilic variants that exhibit neuroprotective/neurotrophic action on, e.g., neurons originating in the central nervous system either in vitro or in vivo. An ADNF-related neuroprotective peptide can range from as short as four to eight amino acids and can have, e.g., between 8-20, 8-50, 10-100, or about 200, 500, or more amino acids. An example of a variant ADNP-related neuroprotective peptide is a 4-amino acid peptide of SKIP (SEQ ID NO: 2), see Amram et al. Sexual Divergence in Microtubule Function: The Novel Intranasal Microtubule Targeting SKIP Normalizes Axonal Transport and Enhances Memory. *Mol Psychiatry*, 2016; 21:1467-76. Another variant, a NAP alpha-aminoisobutyric acid analog, is described in U.S. Pat. No. 8,586,548. Further examples include NAT and TAP described in Gozes et al., *J. Alzheimers Dis.* 2014; 40 Suppl 1:S23-36, as well as all D-amino acid derivatives of SALLRSIPA (SEQ ID NO:3) or NAPVSIPQ (SEQ ID NO:1), e.g., Brenneman et al., *J Pharmacol Exp Ther.* 2004 June; 309(3):1190-7. Additional examples include NAP alpha-aminoisobutyric acid (IsoNAP, as above), Gozes et al., *J Mol Neurosci.* 2014 January; 52(1):1-9, NAVSIQ (Asn-Ala-Val-Ser-Ile-Gln) (SEQ ID NO:4) Biswas et al., *ACS Chem Neurosci.* 2015 Aug. 19; 6(8):1309-16. Furthermore, following on NAPVSIPQ-ADNP ("NAPVSIPQ" DISCLOSED AS SEQ ID NO:1) homologous sequences in birds (bioinformatics) including, but not limited to derivatives such as NAPVSLSQ (SEQ ID NO:5) and NTPVSLSQ (SEQ ID NO:6) as well as lipophilic derivatives of all the above, including lipophilic derivatives such as vasoactive intestinal peptide derivatives, SNV, stearyl-KKYL (SEQ ID NO:7) and pituitary adenylate cyclase polypeptide (PACAP) derivatives targeting brain protection (Gozes et al., *Proc Natl Acad Sci USA.* 1996 Jan. 9; 93(1):427-32; Gozes et al., *Proc Natl Acad Sci USA.* 1999 Mar. 30; 96(7):4143-8;

Gozes. *J Mol Neurosci.* 2010 November; 42(3):261-3; Lamine et al., *Neuropharmacology* 2016 September; 108: 440-50; Polanco, et al., *Sci Transl Med.* 2016 Dec. 21; 8(370):370ra181; http://www.isfn.org.il/images/stories/abstracts2016_112.pdf—Sragovich and Gozes)

Various clinical applications of ADNP-related neuroprotective peptides have been reported for the treatment of anxiety, depression, schizophrenia, peripheral neurotoxicity, fetal alcohol syndrome, and a variety of tauopathies, including neurodegeneration such as Alzheimer's disease, Parkinson disease, frontotemporal dementia, amyotrophic lateral sclerosis (ALS) and diabetes associated brain degeneration. ADNP-related neuroprotective peptides have also been shown to be effective for enhancement of memory and learning ability in recipients. See, e.g., U.S. Pat. Nos. 6,933,277; 7,384,908; 7,427,598; 7,452,867; 7,863,247; 7,960,334; 8,067,369; 8,143,221; 8,324,166; 8,586,548; and 8,618,043.

Chlorobutanol Formulation

Chlorobutanol, or trichloro-2-methyl-2-propanol, is a chemical preservative, sedative hypnotic and weak local anaesthetic similar in nature tochloral hydrate. It has antibacterial and antifungal properties. Chlorobutanol is typically used at a concentration of 0.5% where it lends long term stability to multi-ingredient formulations. However, it retains antimicrobial activity at 0.05% in water. In pure state it is a white, volatile solid with a menthol-like odor.

Chlorbutanol is used as an antibacterial preservative, like benzalkonium chloride that is used in the currently available formulation for NAP (davunetide). The preservative is required to maintain functionality of the active ingredient. As chlorobutanol is an alcohol, unlike benzalkonium chloride, it may affect membrane permeability (Hanig et al. Eur J Pharmacol 18, 79-82, 1972). NAP has an intracellular target, namely, microtubule end binding proteins 1 and 3 (EB1 and EB3) (Oz et al. *Mol Psychiatry* 19, 1115-1124, doi:10.1038/mp.2014.97, 2014), and although it freely crosses the cytoplasmic membrane (Divinski et al. J Biol Chem 279, 28531-28538, 2004), enhanced bioavailability is always an advantage. Importantly, chlorobutanol does not disrupt the blood brain barrier, but specifically enhances NAP penetration as shown in our control experiment detailed below.

Importantly, testing chlorobutanol, in comparison to benzalkonium chloride in terms of corneal permeability, suggested the benzalkonium and not chlorobutanol affect corneal permeability, and only benzalkonium chloride adversely affected cell survival (Kusano et al. Cornea 29, 80-85, doi:10.1097/ICO.0b013e3181a3c3e6, 2010). Thus, our finding of enhancement of NAP bioavailability with chlorobutanol is surprising.

Furthermore, nasal delivery of other peptides suggested superiority of benzalkonium over chlorobutanol for the vasopressin analogue desmopressin acetate (DDAVP) tested in vitro to evaluate the effect of the contained preservatives on drug permeation across rabbit nasal mucosa. In the presence of preservatives (e.g., benzalkonium or chlorobutanol), DDAVP permeation in vitro always increased ($p<0.05$), although at different extents (chlorobutanol<benzalkonium<sorbate). While for benzalkonium structural damage of the mucosa could occur decreasing its barrier properties, the effect of sorbate on drug transport was further investigated. After having found that sorbate permeated together with DDAVP, the hypothesis that the two compounds formed an ion pair in solution with improved permeability was made. Additional experiments with aqueous test solutions reconstructed ad hoc containing desmopressin and varying sorbate concentrations confirmed the enhancing effect of sorbate, which however resulted to be independent of sorbate concentration. Thus, preservatives significantly enhanced desmopressin permeation in vitro across rabbit nasal mucosa with different mechanisms (Bortolotti et al., European journal of pharmaceutical sciences: official journal of the European Federation for Pharmaceutical Sciences 37, 36-42, doi:10.1016/j.ejps.2008.12.015, 2009). Our current results indicate that, surprisingly, with NAP, chlorobutanol is much more effective for brain bioavailability. Importantly, in nasal formulations, chlorobutanol is described as bacterial inhibitor, e.g., in nasal delivery of analgesic ketorolac tromethamine thermo- and ion-sensitive in situ hydrogels, sulfobutyl ether-β-cyclodextrin of 2.5% (w/v) and chlorobutanol of 0.5% (w/v) were chosen as the penetration enhancer and the bacterial inhibitor, respectively (Li et al., International journal of pharmaceutics 489, 252-260, doi:10.1016/j.ijpharm.2015.05.009, 2015).

Interestingly, we have discovered differences in axonal transport between males and female mice—in the olfactory bulb (Amram et al. *Mol Psychiatry,* 2016; 21(10):1467-76), with faster rate in females. These findings require further evaluation of male-female differences in intranasal application as well as pipeline compounds including SKIP (SEQ ID NO:2).

We have further tested if chlorobutanol breaks up the blood brain barrier and showed that it does not, however it facilitate NAP absorption. The experimental details are provided below:

Evans blue detection (a marker for blood brain barrier intactness) in brains of pretreated ICR female (5-month-old) mice with chlorobutanol: Chlorobutanol formulation was administered intranasaly (5 ul/nostril). Control animals received saline. 2 hours after nasal administration, 2% Evans blue (4 ml/kg, 130ul/30 gr mouse) were injected IP. 2 hours after Evans blue injection, animals were sacrificed. Animals were perfused with ice-cold saline through the left ventricle for 20 min to remove residual intravascular agent. The brains were remove for dissection and assays. Quantitative evaluation of Evans blue dye was performed using a previously published method (Uyama et al., J Cereb Blood Flow Metab 8, 282-284, doi:10.1038/jcbfm.1988.59, 1988). Briefly, each tissue sample was weighed, homogenized in a three-fold volume of 50% trichloroacetic acid (wt/volume) solution (6.1 N solution; Sigma), and centrifuged at 10000 r.p.m. for 20 min. The supernatants were diluted with ethanol (1:3), and fluorescence was quantified by using a microplate fluorescence reader (Victor2-V multilabel plate reader, PerkinElmer, Wellesley, Mass., USA) (excitation: 620 nm, emission: 680 nm). Sample value calculations were based on Evans blue dye standards mixed with the same solvent (50-3200 ng/ml). Results were expressed in nanograms of Evans blue dye per milligram of tissue. Results showed no significant penetration of Evans blue (<0.1 ng/ml. which was the limit of detection) and no difference between chlorobutanol and saline, meaning that the blood brain barrier remained intact.

Intranasal NAP (NAPVSIPQ, SEQ ID NO:1) also called davunetide protected against cognitive impairment in mice and men. Comparing water based formulation including the preservative benzalkonium chloride DD=(7.5 mg NaCl, 1.7 mg citric acid monohydrate, 3 mg disodium phosphate dihyrate, 50% 1 mg benzalkonium chloride in 1 ml solution) to a simplified formulation containing the preservative chlorobutanol CB=(0.25% chlorobutanol, 0.85% NaCl, pH=3.5 or 4.0) revealed a surprising .about.4 fold increase in brain bioavailability, and a dramatic concentration in brain vs.

body for NAP in chlorobutanol. To assess if NAP in chlorobutanol also provided neuroprotection, the improved formulation was tested in an Adnp-deficient mouse model depicting brain damage and behavioral deficits associated with ADNP-related autism. ADNP (activity-dependent neuroprotective protein), is the parent protein of NAP, and NAP enhances ADNP association with microtubule end binding proteins, thus protecting axonal transport (Amram et al., Mol Psychiatry. 2016 October; 21 (10):1467-76; Ivashko-Pachima et al., Mol. Psychiatry. 2017, in press). We show here that Adnp-deficiency in the mouse is not only associated with learning and memory and social deficits, but also with deficits in brain structure as detected by diffusion tensor imaging. These behavioral and structural deficits were ameliorated by NAP-chlorbutanol treatment as well as by NAP-DD (benzalkonium) treatment. Additionally, Adnp deficiency resulted in significantly reduced vocalization in the pups and amelioration by NAP treatment. Given the involvement of ADNP in prevalent neurological/neuropsychiatric diseases including autism (Gozes et al., J Mol Neurosci. 2015 August; 56 (4):751-7), developmental retardation, in general, bipolar disorder, schizophrenia, aging associated mild cognitive impairment and Alzheimer's disease, these findings indicate a broad field of clinical applications for NAP and pipeline products.

EXAMPLES

The following examples are provided by way of illustration only and not by way of limitation. Those of skill in the art will readily recognize a variety of non-critical parameters that could be changed or modified to yield essentially the same or similar results.

Introduction

The neuroprotective drug candidate, NAP (NAPVSIPQ, SEQ ID NO:1) also called davunetide, was derived from activity-dependent neuroprotective protein (ADNP) by structure activity screening (1). Our most recent results identified the shared target of NAP and ADNP, that is dependent on the shared SIP domain, namely, microtubule end binding proteins EB1 and EB3 (2). NAP enhanced ADNP-EB3 interaction to promote dendritic spine formation and synaptic plasticity. Furthermore, NAP enhanced ADNP-microtubule associated protein 1 light chain 3 (LC3) interaction (3) thus protecting essential cellular/neuronal protective mechanisms such as axonal transport (4) autophagy (5)/and inhibiting apoptosis (6). In this respect, Adnp deficiency in mice resulted in impaired axonal transport which was ameliorated by the NAP active modified fragment SKIP (7).

NAP showed neuroprotection in mouse models of chronic neurodegeneration such as Alzheimer's disease (8-10), Parkinson disease (11, 12), frontotemporal dementia (13), amyotrophic lateral sclerosis (ALS) (4) and diabetes associated brain degeneration, suggestive as a risk factor for Alzheimer's disease (14). All these disease are characterized by progressive neuronal cell death that is linked to deterioration of the microtubule system [e.g. (15)].

Interestingly, the microtubule system is also deficient in psychiatric diseases, such as schizophrenia and NAP has shown protection against cognitive deficits in two microtubule-associated mouse models of schizophrenia namely, the microtubule-associated protein 6 deficient (Map6$^{+/-}$) mouse (16, 17) and the mutated disrupted in schizophrenia 1 (DISCI) 1) mouse (18).

Importantly, NAP also protected against acute brain injury (at the time of injury) in mouse models of head trauma (19, 20), stroke (21), epilepsy (22) and fetal alcohol syndrome [e.g. (23)], providing long-lasting effects [e.g. (24)].

Together, these studies attest to a broad range of preclinical efficacy, holding a promise for clinical efficacy. Indeed, in clinical studies, NAP (davunetide) showed efficacy in two independent studies, namely, increase in cognitive scores in amnestic mild cognitive impairment patients (25, 26) and protection of functional activities of daily living in schizophrenia patients (27) coupled to brain neuroprotection (28). In a study in severely affected individuals suffering from progressive supranuclear palsy (PSP), belonging to the family of rapidly progressing frontotemporal neurodegenerations, NAP (davunetide) did not show efficacy (29). In this trial, the patients were treated with 30 mg NAP (davunetide) twice daily and this dose required a change in the formulation, namely reduction of the ionic strength and the concentration of the preservative, which raises a question of potential limited bioavailability in this patient population.

For chronic non-invasive nasal NAP administration, we routinely used (7.5 mg NaCl, 1.7 mg citric acid monohydrate, 3 mg disodium phosphate dihyrate, 50% 1 mg benzalkonium chloride in 1 ml solution), (30), which yields significant brain bioavailability (31-33). In the current study, we simplified the excipient and exchanged the benzalkonium chloride (a preservative) with chlorobutanol (0.25% chlorobutanol, 0.85% NaCl, pH=3.5 or 4.0) revealing a surprising ~4 fold increase in brain bioavailability, and a dramatic concentration in brain vs. body for NAP in chlorobutanol.

To assess if NAP in chlorobutanol also provided neuroprotection, the improved formulation was tested in an Adnp-deficient mouse model depicting brain damage and behavioral deficits. While complete Adnp deficiency in mice is lethal and the brain does not form (34), the Adnp mouse is viable and suffers brain damage and cognitive deficiencies, in a sex-dependent manner (7, 35-37).

In the human population, de novo mutations were recently identified in ADNP, in children with autism spectrum disorder with cognitive disabilities (38, 39). In the adult and aging population, ADNP and the sister ADNP2 transcripts are deregulated in the postmortem schizophrenia hippocampus (40). In lymphocytes, ADNP and ADNP2 transcript levels can serve as biomarkers for schizophrenia (3) and Alzheimer's disease (41). ADNP levels in the plasma are significantly correlated with IQ (42). ADNP single polynucleotide polymorphism (SNPs) have been associated with bipolar disorder with comorbid eating disorder [e.g. rs6096154 (C/T); rs6020824 (C/T); rs1062651 (A/G)] (43).

In terms of genes regulated/associated by/to ADNP, 1] de novo mutations in the ADNP-binding CBX5 (HP 1-alpha) (44, 45) have been linked to schizophrenia (associated with very young or old paternal age, CBX5, D10A, missense Mutation) (46). 2] ADNP regulates calcium channel expression (7). Specifically, ADNP regulates CACNA1C in a sex-dependent manner (7) (Table 1). In schizophrenia-spectrum affected males, rs10774035 minor allele (T) carriers had higher Global Assessment of Functioning (GAF) scores at three time points (premorbid, worst ever, current). In contrast, females carrying rs10774035 minor alleles had impaired recovery from schizophrenia-spectrum episodes (47). Furthermore, ADNP regulates the expression of apolipoprotein E (APOE), the major risk gene for Alzheimer's disease, in a sex-dependent manner (37, 45).

Together, this involvement of ADNP in autism, schizophrenia and Alzheimer's disease, makes the Adnp-deficient mouse model (Adnp$^{+/-}$) an interesting model for further studies of drug efficacy. Here, NAP-chlorobutanol-treatment provided highly significant protection. Given the broad association of ADNP with human brain disease, we foresee a wide range of clinical application for the new NAP-davunetide-chlorobutanol as well as benzalkonium formulations as well as pipeline products (7) and ADNP-regulating compounds (e.g. (48)).

Materials and Methods

Materials

NAP (NAPVSIPQ, SEQ ID NO:1) was synthesized as before [e.g., (18)]. For bioavailability studies, NAP was labeled with cy 5.0 on the amino terminal site in the lab of prof. Doron Shabat from the school of chemistry (Tel Aviv University). The labeled peptide was dissolved in 1.times.DD/ml solution (7.5 mg NaCl, 1.7 mg citric acid monohydrate, 3 mg disodium phosphate dihyrate, 50% 1 mg benzalkonium chloride in 1 ml solution) or in chlorobutanol solution containing 0.25% chlorobutanol, 0.85% NaCl, pH=3.5 or 4.0.

Chlorobutanol (designated below as CB): is a well-accepted, widely used, very effective preservative in many pharmaceuticals and cosmetic products, e.g. injections, ointments, products for eyes, ears and nose, dental preparations, etc. It has antibacterial and antifungal properties and has been used for more than 125 years when it was first manufactured. Chlorobutanol is typically used at a concentration of 0.5% where it lends long term stability to multi-ingredient formulations (48). Chemical formula: Hemihydrate: $C_4H_7CI_3O \cdot 1/2\ H_2O$, Anhydrous: $C_4H_7CI_3O$. Formula Weight: Hemihydrate: 186.47, Anhydrous: 177.46

Slightly soluble in water; soluble in 0.6 of alcohol; freely soluble in chloroform; very soluble in ether; soluble in glycerol (85%). Soluble 1 in 125 of water, 1 in 1 of alcohol, and 1 in 1 10 of glycerol; freely soluble in ether; in chloroform, and in volatile oils. This product is stable at ambient temperatures and atmospheric pressures for a period of 5 years (Hemihydrate) or 3 years (Anhydrous). Chlorobutanol has antibacterial and fungicidal effects and it is used at a concentration of 0.5% as a preservative in injections, eye drops and mouth washes, salves, creams and ointments as well as cosmetics.

Chlorobutanol is widely used as a preservative in a number of pharmaceutical formulations, particularly ophthalmic preparations. Although animal studies have suggested that Chlorobutanol may be harmful to the eye, in practice the widespread use of Chlorobutanol as a preservative in ophthalmic preparations has been associated with few reports of adverse reactions. The incidence of toxicity is low. The acute oral LD50 is 510 mg/kg in rats. The acute dermal LD50 is greater than 2000 mg/kg in rabbits. A single dermal application of 2000 mg/kg produced 10% mortality but no signs of toxicity. May cause irritation. Topical application may cause mild anesthesia of the skin. Local effects included a mild moderate erythema (redness). Rarely, sensitization reactions may occur in previously exposed individuals. Non-irritant to rabbit skin following a 24 hour exposure.

The preferred formulation described is comprised of 0.25% weight/weight of chlorobutanol, 0.85% sodium chloride, and 98.86% purified water, and the pH is about 3.5 or 4.0.

Methods

In Animal Imaging Assessing Immediate Brain Bioavailability 8 weeks old female ICR mice were anesthetized by intraperitoneal injection of 10% Ketamine, 5% Xylazine in saline (0.1 ml/10 gr). Sedation maintains after 60 min with subcutane injection of 20% Ketamine (0.5 ml/10 gr). After intranasal application of 0.1 mg/6ul, (DD or Chlorobutanol vehicles), the mice were placed in the Maestro machine (Cri Maestro™ in vivo imaging system, a product of Cambridge Research & Instrumentation, Inc. CRi 35-B, Woburn, Mass., USA). Light emission was measured every 15 min. Measures were taken for 2 hours, after which, the animals were sacrificed, brains were removed and placed in the Maestro for measurements of light emission (excitation=670 nm, emission=700 nm).

Behavioral Measurements in the $Adnp^{+/-}$ Mice

Experiments performed as we described in Malishkevich et al., 2015 (37) and Amram et al., *Mol Psychiatry.* 2016 October; 21(10):1467-76 (7). 3-6 month-old male mice were used, drug application (0.5 µg/5 µl/mouse) was once daily, for one month and then behavioral assays were initiated together with drug application. In experiments with the vehicle termed DD (NAP-benzalkonium), drug application was at 2 months of age and continued as above. Open field experiments (16, 17) and elevated plus maze evaluations (18) were carried out as before.

Magnetic Resonance Imaging (MRI) Assessing Chronically Treated Brains

MRI was performed on a 7.0 T/30 spectrometer (Bruker, Rheinstetten, Germany) using a volume coil for excitation and a rat quadrature coil for acquisition. The MRI protocols included coronal T2 and diffusion tensor imaging (DTI). T2 weighted images obtained with RARE sequence, with repetition time=3000 msec and echo time=49 msec, RARE factor 8, 4 averages, field of view of 2×2 cm, matrix dimensions of 256×256 and 24 slices of 0.5 mm thickness with no gap. The 24 coronal sections were used for volumetric analysis of the whole brain, Lateral ventricle and Hippocampus. DTI was obtained using a diffusion-weighted (DW) spin-echo echo-planar-imaging (EPI) pulse sequence with the following parameters: TR/TE=4000/25 ms, Δ/δ=10/4.5 ms, 4 EPI segments and 32 non-collinear gradient directions with a single b value (1000 sec/mm$^2$) and two images with b value of 0 sec/mm2 (referred to as b0). Geometrical parameters were: 24 slices of 0.5 mm thickness, matrix size of 128×128 and FOV of 20 mm$^2$). The imaging protocol was repeated 3 times for signal averaging and to compensate for acquisition where significant head motion was observed. Image analysis included DTI analysis of the DW-EPI images to produce the FA, radial, and axial diffusivity indexed maps.

Additional Outcome Measures for Adnp Deficiency and NAP Protection:

Stem Cell Proliferation

A potential explanation for changes in MRI/DTI results could be changes in stem cell proliferation and differentiation. To test for differences in stem cell proliferation, bromo deoxy uridine (BRDU) treatments and immunohistochemical analyses of $Adnp^{+/-}$ mouse brains compared to $Adnp^{+/+}$ brains were carried out. 2 month old mice (heterozygous and littermates, both sexes) were injected with a short protocol of BRDU as followed: four injections of 2 mg BRDU/100 µl PBS/mouse (~30 g), every two hours and underwent perfusion within one hour from the last injection. The perfusion was performed transcardially, under deep anesthesia with 4% paraformaldehyde (4% PFA, pH 7.4), brains were removed, post-fixed and embedded in paraffin. The fixed brains were shipped to Nikolaos C. Grigoriadis laboratory (Aristotle University of Thessaloniki, Greece) and immunohistochemical procedures with BRDU-markers were performed (7). Sections were examined under Zeiss optical microscope focusing on the hippocampus and the prefrontal cortex areas and measurements were expressed as positive cells per mm². For NAP and NAP-derived peptides effect on stem cells, we have started treating mouse pups with NAP during 1-14 days of life (35, 49) (see below), labeling with BRDU and perfusion at two months of age (coherent to previous untreated mice).

Gene Expression

Quantitative reverse transcription real time polymerase chain reaction (RT-PCR) was performed as before (18, 37).

Ultrasonic Vocalization

Language and speech deficits affect ADNP-mutated children (38, 39) and autistic children in general (51). In rodents, both speech and social communication are tested by analysis of isolation induced ultrasonic vocalizations (USVs) (52). As part of USV test, 25 µg of NAP were diluted in 1 ml saline and injected (subcutaneous) to Adnp$^{+/-}$ mouse pups for 9 subsequent days (1-9 days of age) in doses of 20, 40 µl on days 1-4, 5-7 respectively (50).

Results

Chlorobutanol (CB) Surprisingly Enhances Brain Penetration

FIG. 1A shows the surprising result of enhanced brain/body bioavailability in the presence of the new vehicle, chlorobutanol (CB) over time. FIG. 1B shows the surprising finding of enhanced brain bioavailability by picture evaluation. FIG. 1C shows quantitative assessment of 3 independent experiments, showing the surprising 4-fold increase in specific brain bioavailability. As chlorobutanol is used in eye drops and in ointments, similar increased bioavailability is expected by other topical routes of administration, although initial results suggest similar skin bioavailability.

Figure 2C:
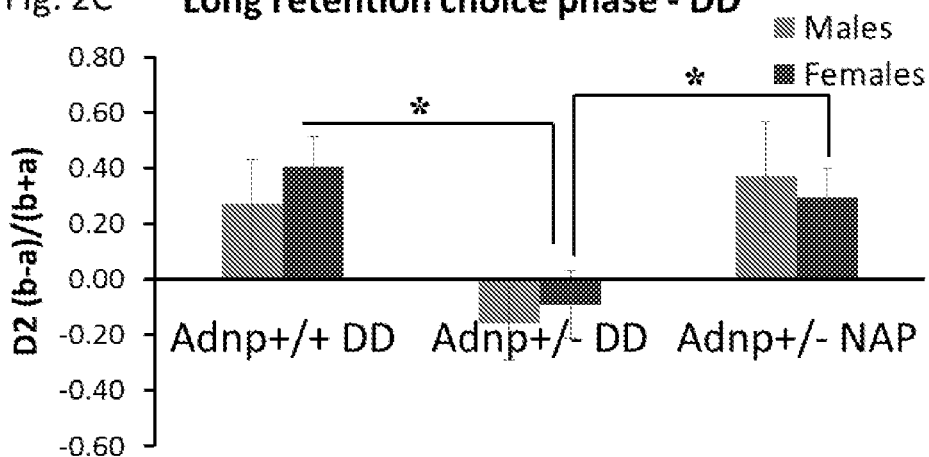

NAP—New Formulation Treatment Increases the Relative Discrimination Between Novel and Familiar Objects and Further Increases Social Memory Animal performance in the object recognition memory test is shown. Two identical objects were presented during the habituation phase, and one of the identical objects was replaced by a novel object during the short retention choice phase (3 hours) and the long retention choice phase (24 hours). Adnp$^{+/-}$ mice compared to Adnp$^{+/+}$ mice spent significantly shorter time periods in exploring the new objects, indicative of impaired memory, NAP-CB intranasal treatment completely ameliorated this impairment (FIG. 2A,B). In the long retention choice test and in younger mice, NAP-DD also protected, significantly in females (FIG. 2C). Similarly, NAP-CB treatment completely protected social memory (FIG. 3A). Experiments were repeated in males and females showing the same outcome, with NAP-DD treated mice exhibiting almost similar data in females and less significant in males (FIG. 3B,C). Olfaction was also measured showing a general change in olfactory behavior which is genotype, sex and nasal formulation-specific and which is apparently normalized by NAP treatment (FIG. 3D-G).

NAP—New Formulation Treatment Protects Against Increased Anxiety in the Adnp-Deficient Model Experiments were performed as described (18), assessing the different times spent in open arms (indicative of exploratory behavior) versus closed arms (indicative of anxious behavior) in the elevated plus maze (FIG. 4).

Figure 5A:
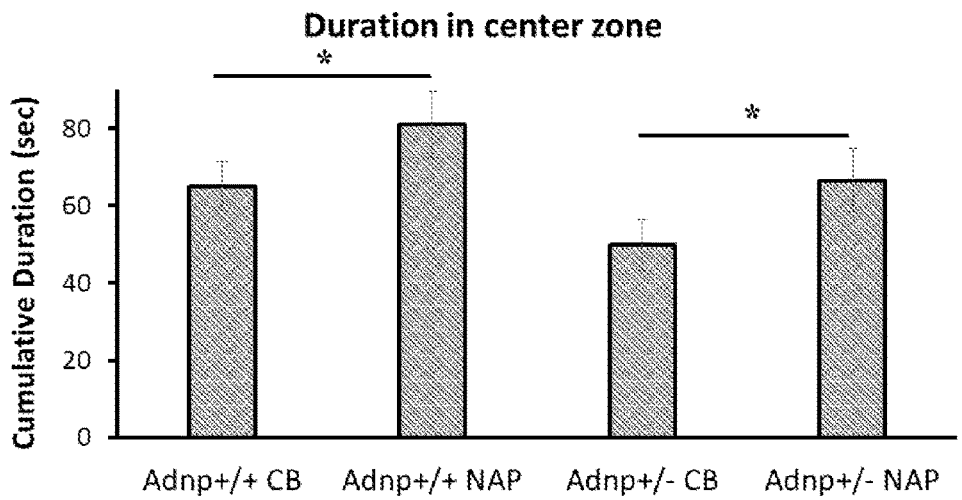
Figure 5B:
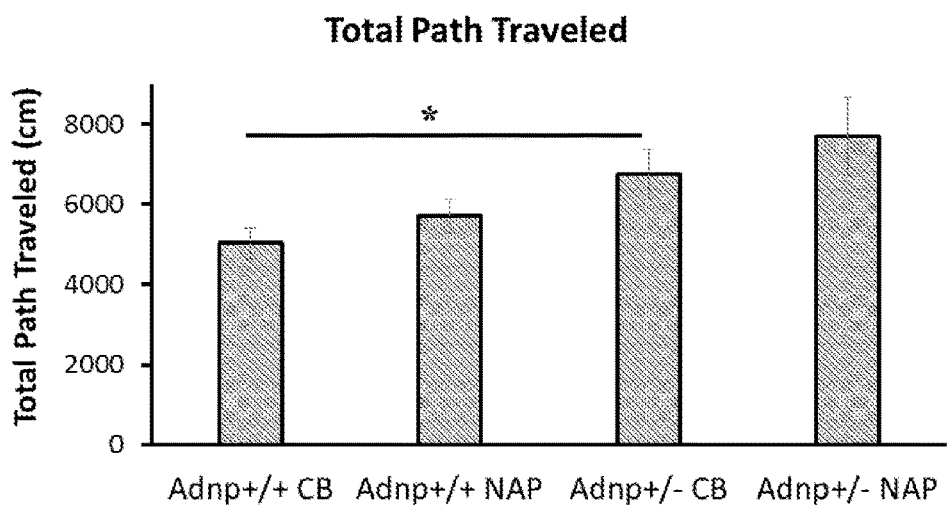
Figure 5C:
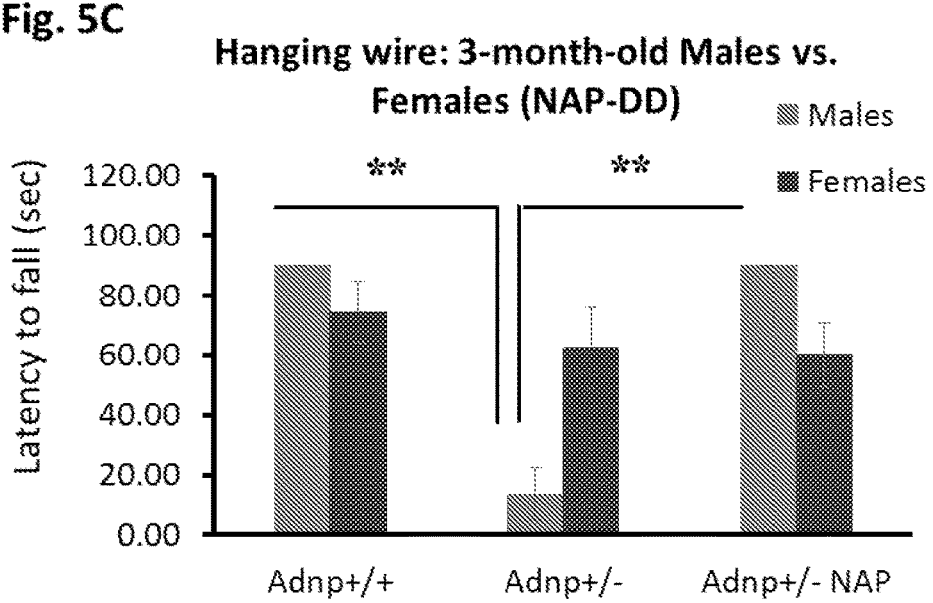

The reduction of anxious behavior by NAP treatment was also visible in the open field test (performed as before) (16), with treated mice staying longer time at the center of the field (FIG. 5A), but with the treatment not affecting the slight hyperactivity, which was observed in the Adnp$^{+/-}$ mice (FIG. 5B). Two additional tests were performed, namely, hanging wire test (FIG. 5C,D) and grip strength test (FIG. 5E,F). Surprisingly, NAP significantly increased grip force only at 3 months of age in the NAP-DD-treated mice.

Structural Changes in the Adnp Brain and Amelioration by NAP Treatment

Mean Diffusivity (MD) is an inverse measure of the membrane density. MD is sensitive to cellularity, edema, and necrosis. Increased MD means increased damage. NAP-CB treatment protected against increased hippocampal diffusivity in the Adnp mice (FIG. 6A). Fractional Anisotropy (FA) is a summary measure of microstructural integrity. While FA is highly sensitive to microstructural changes, it is less specific to the type of change. FIG. 6B shows the FA data implicating Adnp deficiency in structural impairment and improvement by NAP-CB treatment.

Stem Cell Proliferation

FIG. 7 shows that Adnp$^{+/-}$ male mice exhibited significantly less BRDU staining in prefrontal cortex, compared to Adnp$^{+/+}$ mice. In contrast, Adnp females showed only a reduction trend in the dentate gyrus. The results in the males agree with our MRI data showing brain impairment in the Adnp-deficient mice (see above).

Vocalization: NAP Protects Against Changes in Vocalization

Figure 8F:
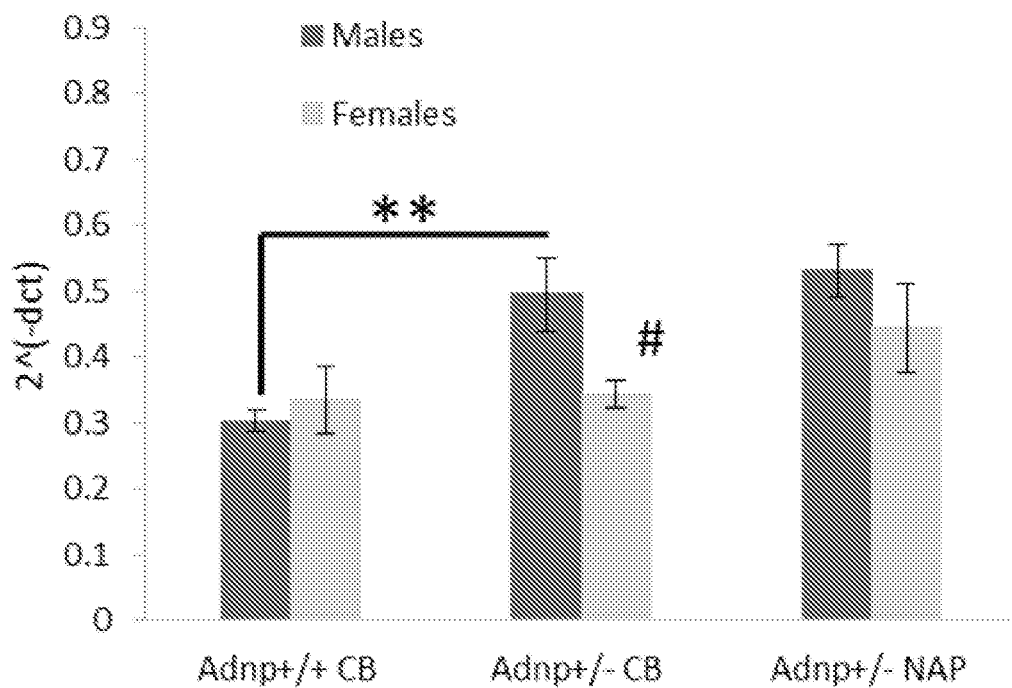

A major impediment in the ADNP-mutated children is slow development or lack of spoken language (38). Our previous results have shown that NAP protects against deficiencies in the major language gene expression Foxp2 in mice (18). We have now extended these findings to show that Foxp2 is dysregulated in the Adnp-deficient mouse model (FIG. 8A, hippocampus, FIG. 8B, tongue). Furthermore, NAP was shown to correct the impediment of changes in Adnp expression in the tongue. The experiments were further extended to additional genes that are dysregulated in terms of ADNP autism-related mutations (Gozes et al., Translational Psychiatry, under review) and results have shown amelioration by NAP for Akap6, in the tongue (FIG. 8 C,D). Interestingly, FIG. 8 E, F shows that Akap6 is also deregulated in the hippocampus of the Adnp haploinsufficient female mouse (trend) and this is ameliorated by NAP treatment, while Chl1, which is regulated by ADNP mutations in humans (Gozes et al., Translational Psychiatry, in review) is also regulated by NAP (FIG. 8F). In this respect, CHL1 as well as other genes/proteins, which are regulated by ADNP/NAP are also found in serum/plasma and can be used as markers for efficacy. Importantly, we have now adapted technologies to test "language impediment" in mice, namely, recording the number and duration of USVs from 6-9 days old mouse pups, following dam-separation (53). This feature characterizes mouse pups and tend to disappear by the age of 13 days, following the opening of the ear canals and the acquisition of vision (54). Results of the number of USVs produced during a minute measuring period revealed statistically significant difference between male+ female Adnp and Adnp$^{+/+}$ littermates. Furthermore, NAP treatment protected against this deficiency, normalizing it in females (FIG. 9A-C), addressing a new outcome for NAP treatment in affected populations. FIG. 9D suggests an effect of ADNP on the auditory brain response (ABR).

Protecting the Microtubules: NAP Protects Microtubules Against ADNP Mutations

Looking at ADNP mutations in tissue culture in terms of effects on microtubule dynamics revealed changes that were ameliorated, in part, by NAP treatment (FIG. 10) (for methodology, please see Ivashko-Pachima et al., Molecular Psychiatry, 2017, in press).

Discussion

We show here, for the first time, surprising results that changing the preservative in the NAP (davunetide) formulation (NAP-CB vs. NAP-benzaokonium) resulted in: 1] brain vs. body concentration and 2] 4-fold increase in brain bioavailability compared to the routinely used placebo, benzalkonium chloride. As the chlorobutanol preservative is used in men for >125 years in other formulation for versatile uses, including nasal administration, the transition to clinical application is immediate. NAP-CB treatment resulted in complete amelioration of Adnp-deficient cognitive deficits measured by the object recognition and the social memory tests. Regarding the social memory test, this was not always achieved by NAP treatment, as previous tests with the bezalkonium chloride formulation (NAP-DD) did not show efficacy for NAP in this particular test in a rodent model of diabetes associated cognitive damage (55).

However, results presented here showed that some of the outcomes are age-dependent, sex-dependent and genotype dependent, which may rely on differences in gene expression (see also Amram et al., 2016; Gozes 2017). Furthermore, NAP-DD is also efficacious, especially when looking at young mice in terms of grip strength.

The results went beyond behavioral outcomes to measured changes in DTI, revealing significant NAP protection of brain matter, which could be further extended to measures of connectivity grey and white matter intactness, also relevant to myelin damage and easily implemented in clinical trials. In this respect, Adnp-deficiency has been associated with myelin formation in mice and men (56, 57). The changes in MRI could also be associated with differential stem cell proliferation in the brain, which could be measured in the rodent model by BRDU incorporation, and could be translated into NAP protection of resident brain stem cells.

As indicated above, ADNP mutations in children are associated with impaired language acquisition, and our results here showed that the major gene regulating language acquisition, Foxp2, is deregulated in the hippocampus of the Adnp-deficient mouse. Furthermore, we have shown that NAP normalized Foxp2 expression in a DISCI mutated transgenic mouse model of schizophrenia (18). A recent study revealed a link between DISCI (also associated, like ADNP, with the SWI/SNF complex (58)) and Forkhead –BOX P2 (FOXP2), the gene associated with human ability to acquire spoken language, with FOXP2 regulating DISCI transcripts (59). The FOXP2 protein modulates transcription, consequently influencing the relative abundances of cellular proteins. Mutations in FOXP2 cause developmental disorders that significantly disrupt speech and language skills (60, 61). Although only humans acquire spoken language ability, FOXP2 is well-preserved in animals. Only three amino acids distinguish the human FOXP2 protein from the mouse one. Two of these changes that occurred on the human lineage after separation from the human-chimp common ancestor, are probably responsible for the gap in speaking ability. Recent studies have found that FOXP2 polymorphisms are associated with schizophrenia in human cohorts (62-64). Moreover, SNPs of the FOXP2 gene were identified to be associated with schizophrenia and major depression within the Chinese population (65). Thus, the FOXP2 gene might be involved in the language disturbances found in patients with schizophrenia. During the development of the organism, or in response to the internal/external stimuli, FOXP2 modifies the expression levels of different genes in a tissue-specific manner (66). Our results show that FOXP2 is dysregulated in DISCI mutated mice and NAP treatment normalized FOXP2 expression (18).

Figure 8G:
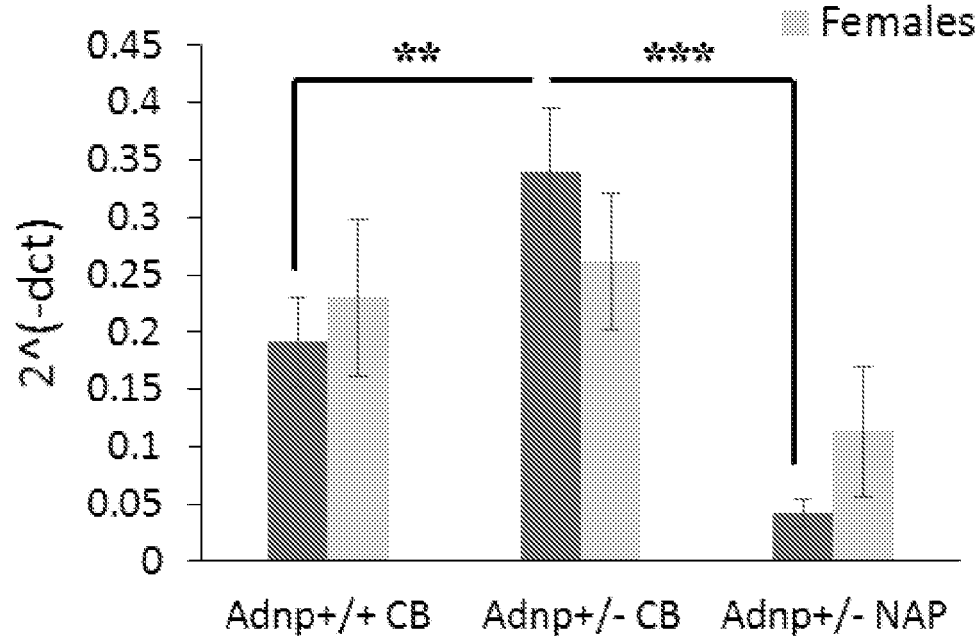
Figure 9A:
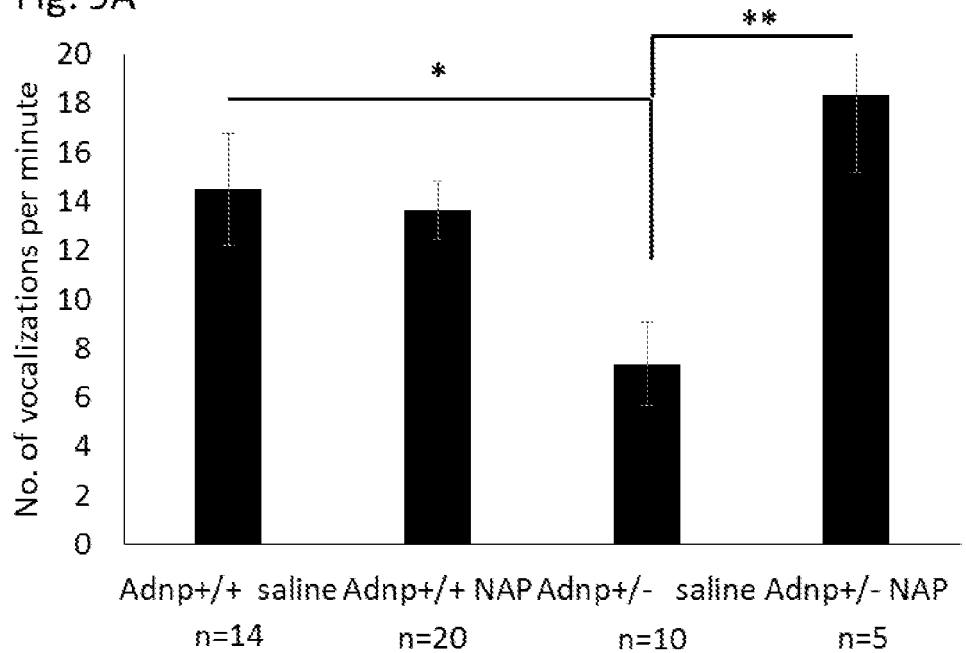
Figure 9B:
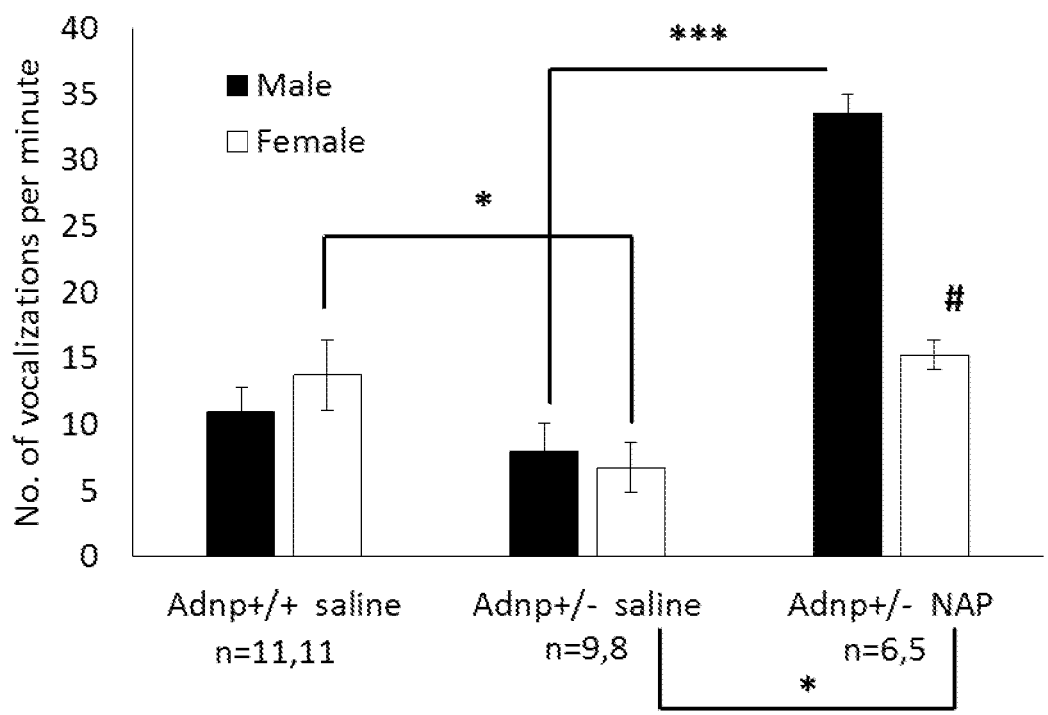
Figure 9C:
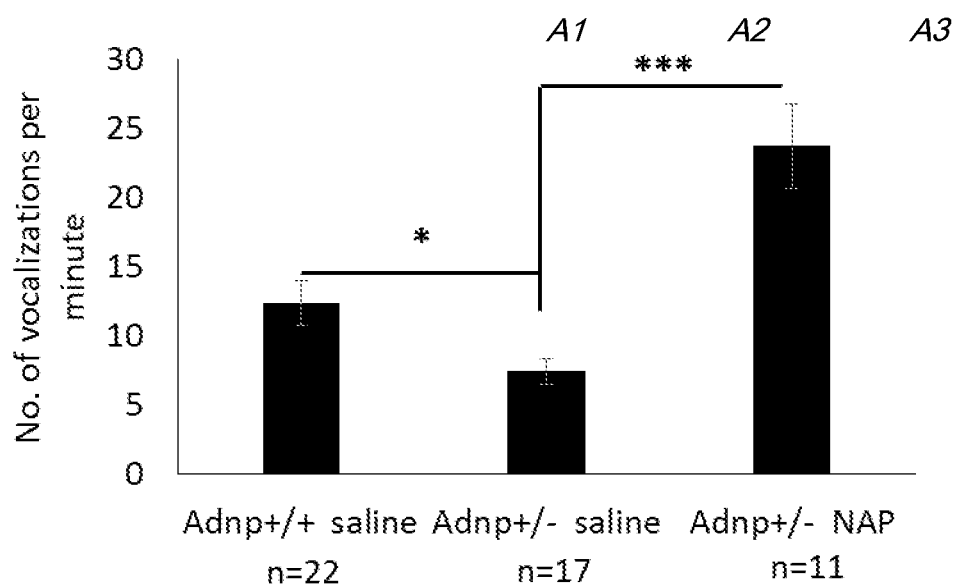
Figure 9D:
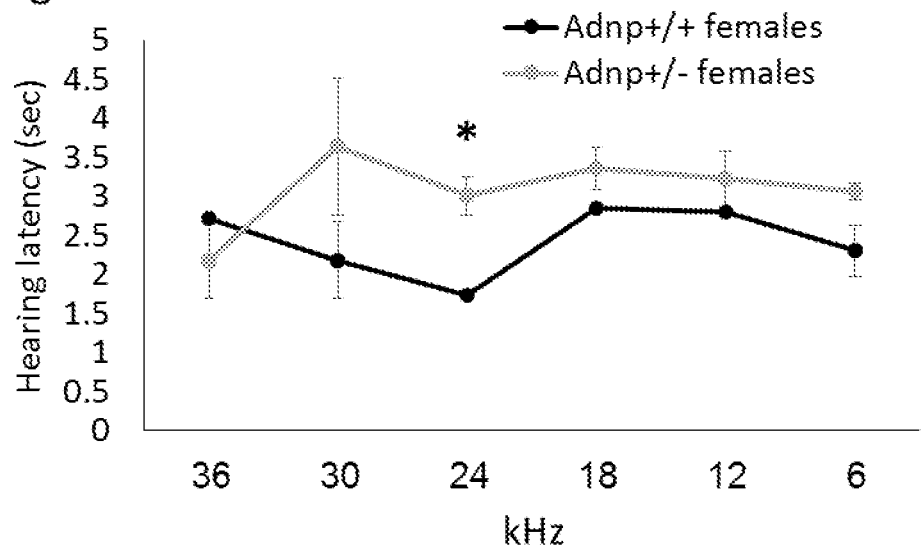
Figure 10B:
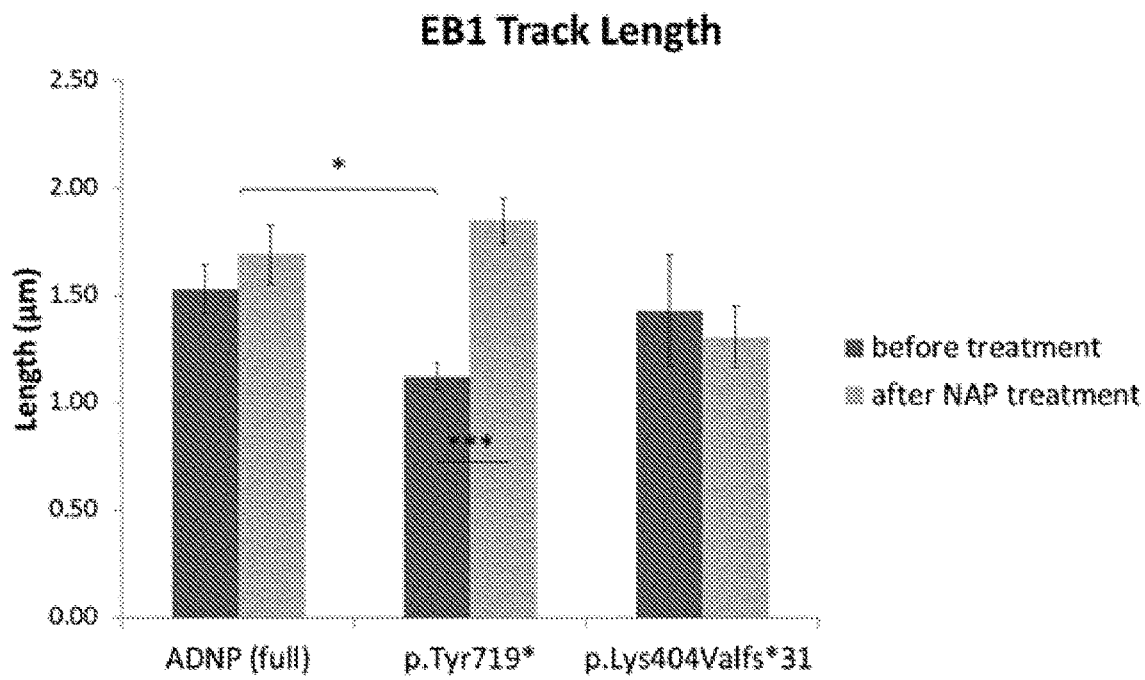
Figure 10C:
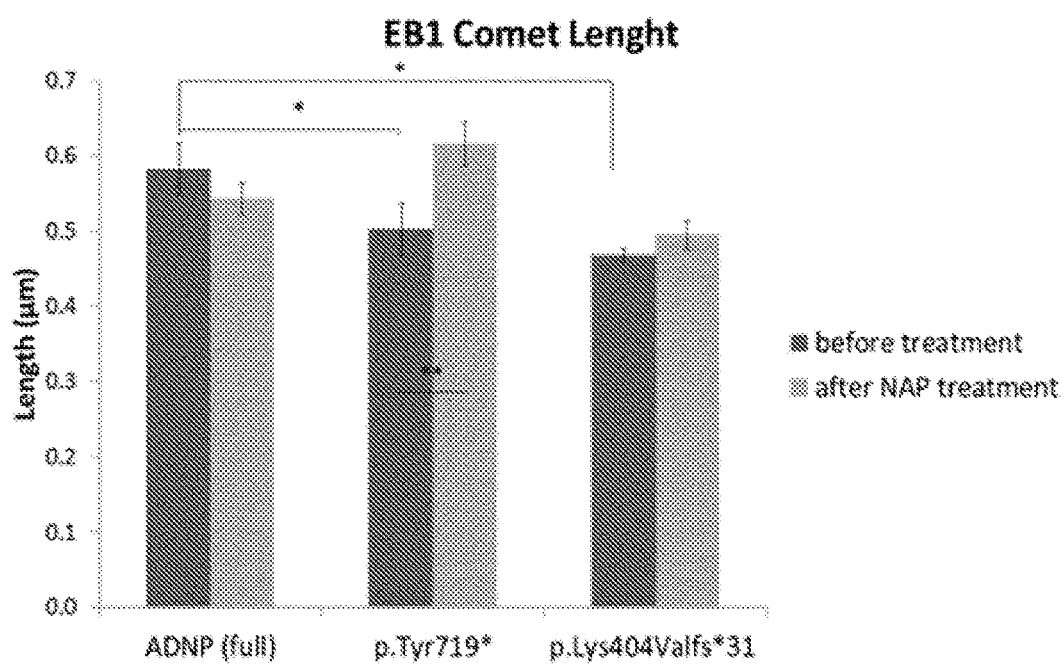
Figure 10D:
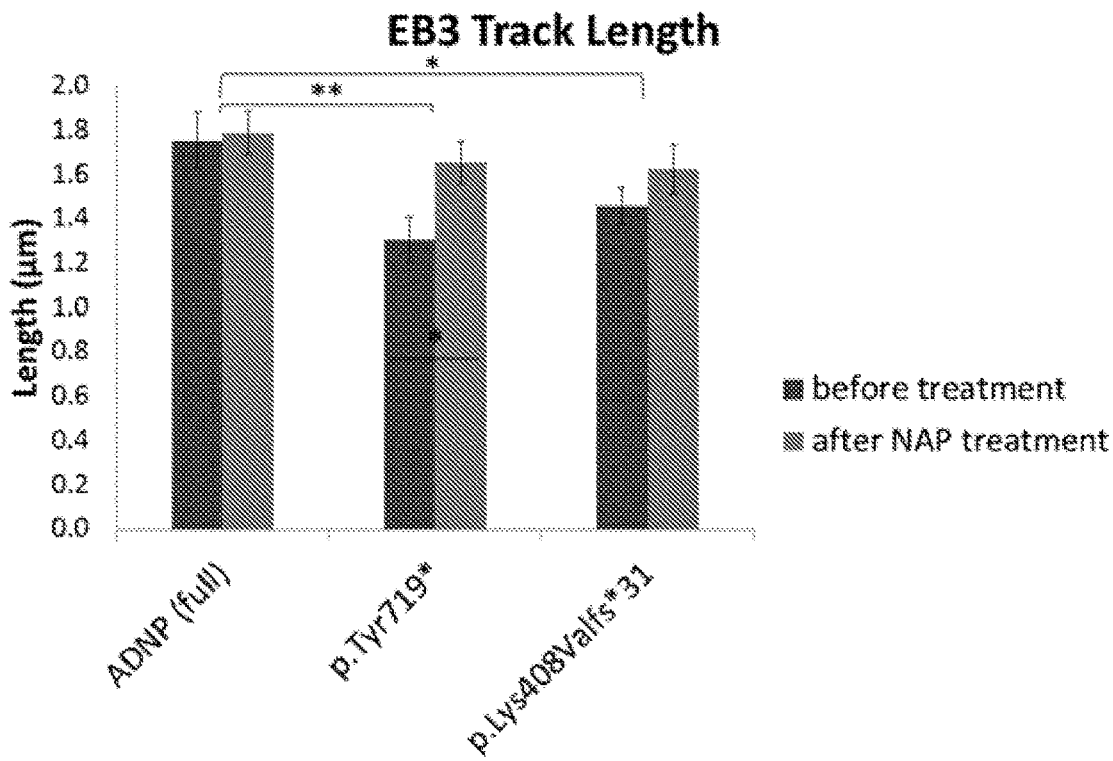
Figure 10E:
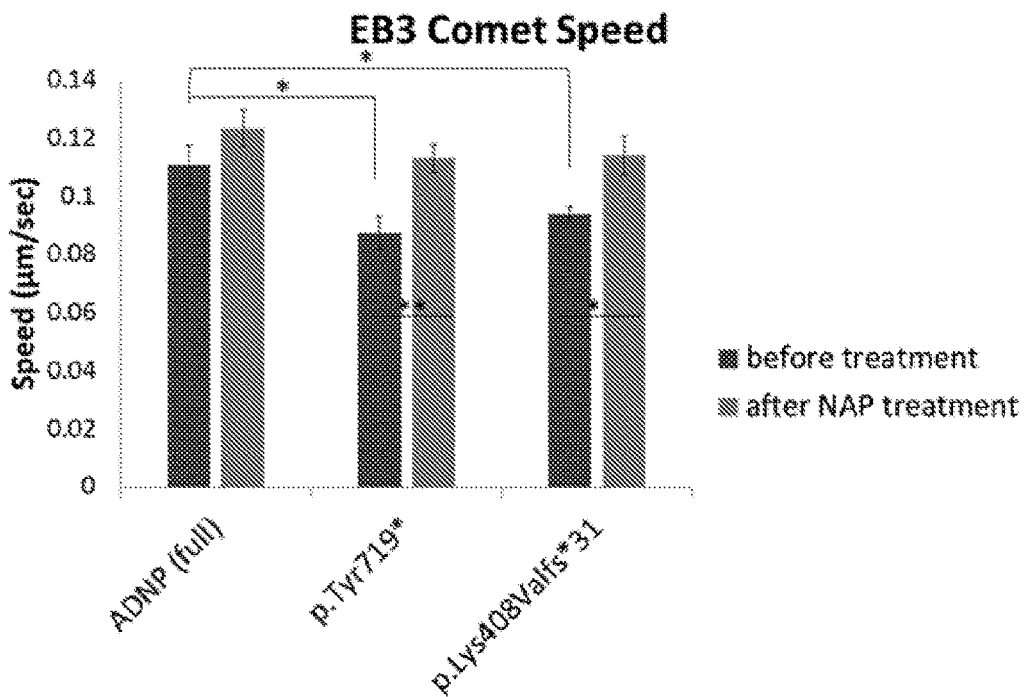
Figure 10F:
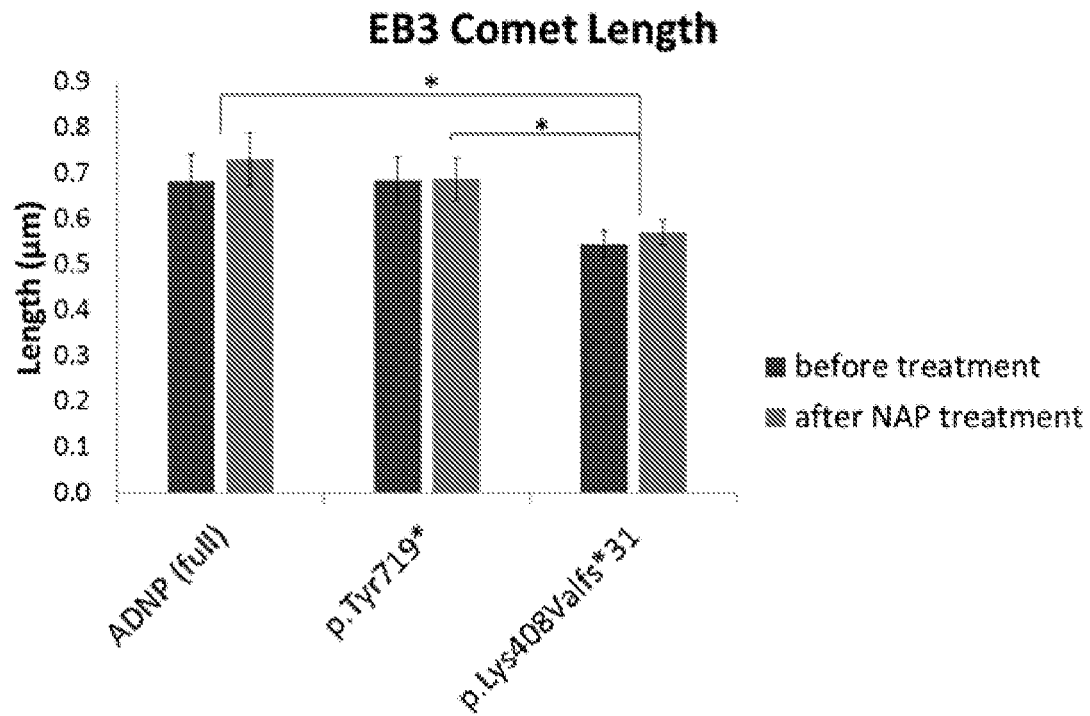
Figure 10G:
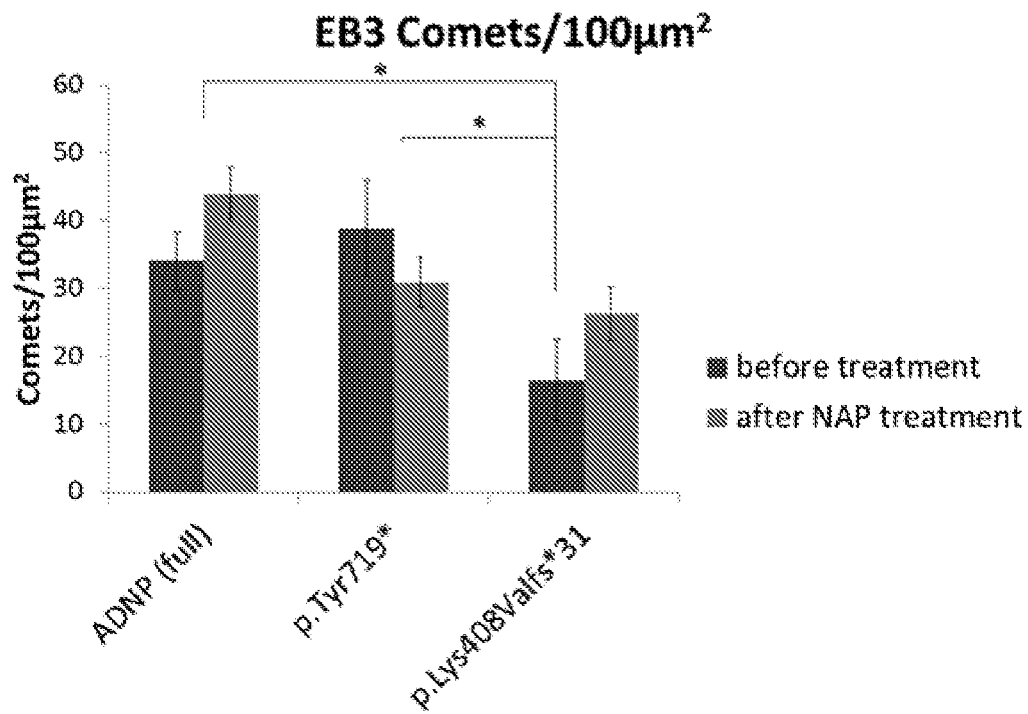

The finding of NAP changing gene expression afflicted by ADNP mutations suggests the possibility of blood borne biomarkers for activity, for example, CHL1 (website: www.sigmaaldrich.com/catalog/product/sigma/rab1365?lang=en®ion=IL) and the result shown for My12 (FIG. 8G).

The de novo mutations identified in ADNP, in children with autism spectrum disorder with cognitive disabilities (38, 39) extend the clinical use of NAP-CB and NAP-DD beyond schizophrenia/autism (27, 28) and Alzheimer's disease (25, 26) to protection against the brain damaging outcome of epilepsy/seizures (22) and attention deficit hyperactivity disorder (website: www.simonsvipconnect.org/en/genetic-changes-were-studying/new-gene-changes/adnp). These findings together with the diagnostic value of blood ADNP in Alzheimer's disease and schizophrenia, the risk ADNP SNPs in bipolar disorder with comorbid eating disorder, the association of ADNP with schizophrenia mutated genes and ADNP regulation of the major risk gene for Alzheimer's disease in a sex-dependent manner (all detailed above) pave the path to patient stratification toward personalized medicine.

The application of NAP-CB goes beyond brain protection. For example, NAP has shown protection in ocular indications of retinal and optic nerve injury (67-69) and chlorbutanol has been used before for eye drops, resulting in less damaging corneal effect compared to benzalkonium chloride (70). This increases the impact of the surprising finding here of chlorobutanol increasing brain permeability over benzalkonium chloride.

Similarly, NAP provided protection against inflammation in a model of Ileitis (70) and the novel formulation may result in better efficacy in inflammatory bowel disease as well other inflammatory diseases, such as arthritis etc. Furthermore, it is conceivable that NAP will protect multiple aspects of the ADNP-related syndrome symptoms as outlined (e.g. (39) and www.adnpkids.com/; rarediseases.info.gov/diseases/12931/adnp-syndrome), including and not limited to fine motor delays, sleep problems, heart and gastric problems, all resulting from delayed synaptogenesis. As these symptoms underlie autism and developmental retardation in general, the scope of the invention is much broader, also given the fact that ADNP is one of the major de novo mutated gene in autism (71, 72).

NAP also provided protection against alcohol intoxication, and we have shown changes in Adnp expression as a consequence of alcohol and cocaine use (Israel Society for Neuroscience, 2015) taking this formulation to protection again drug abuse.

Surprisingly, NAP-benzalkonium chloride was active in young animals, suggesting the possibility of age differences as well as sex and genotype differences with the possibility of usage of different formulations for different indications.

Finally, NAP pipeline products (7) and peptides/drugs/drug candidates in general will benefit from this simplified brain penetrating formulation of chlorobutanol, affecting brain health and meeting unmet, highly prevalent devastating and costly societal needs.

All patents, patent applications, and other publications, including GenBank Accession Numbers, cited in this application are incorporated by reference in the entirety for all purposes.

TABLE 1

Cacna1c expression and effects of the Adnp+/- genotype, Adnp+/, 5 month, 1 month and male females.
Experiments were performed as detailed (2). FC = fold change, pFDR (statistical differences).

| Gene | 5-MONTH-OLD FEMALE ADNP+/- VS. ADNP+/+ | | 5-MONTH-OLD MALE ADNP+/- VS. ADNP+/+ | | 5-MONTH-OLD FEMALE VS. MALE ADNP+/- | | 5-MONTH-OLD FEMALE VS. MALE ADNP+/+ | |
|---|---|---|---|---|---|---|---|---|
| | pFDR | FC | pFDR | FC | pFDR | FC | pFDR | FC |
| Cacna1c | 0.0000 | -2.1707 | 0.1630 | -1.3169 | 0.9679 | 1.1514 | 0.0000 | 1.8979 |

| Gene | 1-MONTH-OLD FEMALE VS. 5-MONTH-OLD ADNP+/- | | 1-MONTH-OLD FEMALE VS. 5-MONTH-OLD ADNP+/+ | | 1-MONTH-OLD MALE VS. 5-MONTH-OLD ADNP+/- | | 1-MONTH-OLD MALE VS. 5-MONTH-OLD ADNP+/+ | |
|---|---|---|---|---|---|---|---|---|
| | pFDR | pFDR | pFDR | FC | pFDR | FC | pFDR | C |
| Cacna1c | 0.0000 | 2.9430 | 0.0240 | 1.3233 | 0.0000 | 3.0544 | 0.0000 | 2.2071 |

REFERENCES

1. Bassan, M., Zamostiano, R., Davidson, A., Pinhasov, A., Giladi, E., Peri, O., Bassan, H., Blat, C., Gibney, G., Glazner, G., Brenneman, D. E., and Gozes, I. 1999. Complete sequence of a novel protein containing a femtomolar-activity-dependent neuroprotective peptide. *J Neurochem* 72:1283-1293.
2. Oz, S., Kapitansky, O., Ivashco-Pachima, Y., Malishkevich, A., Giladi, E., Skalka, N., Rosin-Arbesfeld, R., Mittelman, L., Segev, O., Hirsch, J. A., and Gozes, I. 2014. The NAP motif of activity-dependent neuroprotective protein (ADNP) regulates dendritic spines through microtubule end binding proteins. *Mol Psychiatry* 19:1115-1124.
3. Merenlender-Wagner, A., Malishkevich, A., Shemer, Z., Udawela, M., Gibbons, A., Scarr, E., Dean, B., Levine, J., Agam, G., and Gozes, I. 2015. Autophagy has a key role in the pathophysiology of schizophrenia. *Mol Psychiatry* 20:126-132.
4. Jouroukhin, Y., Ostritsky, R., Assaf, Y., Pelled, G., Giladi, E., and Gozes, I. 2013. NAP (davunetide) modifies disease progression in a mouse model of severe neurodegeneration: protection against impairments in axonal transport. *Neurobiol Dis* 56:79-94.
5. Esteves, A. R., Gozes, I., and Cardoso, S. M. 2014. The rescue of microtubule-dependent traffic recovers mitochondrial function in Parkinson's disease. *Biochim Biophys Acta* 1842:7-21.
6. Idan-Feldman, A., Ostritsky, R., and Gozes, I. 2012. Tau and caspase 3 as targets for neuroprotection. *Int J Alzheimers Dis* 2012:493670.
7. Amram, N., Hacohen Kleiman, G., Sragovisch, S., Malishkevich, A., Katz, J., Touloumi, O., Lagoudaki, R., Grigoriadis, N., Giladi, E., Yeheskel, A., Pasmanik-Chor, M., Jouroukhin, Y., and Gozes, I. 2016. Sexual Divergence in Microtubule Function: The Novel Intranasal Microtubule Targeting SKIP Normalizes Axonal Transport and Enhances Memory. *Mol Psychiatry* In Press.
8. Gozes, I., Giladi, E., Pinhasov, A., Bardea, A., and Brenneman, D. E. 2000. Activity-dependent neurotrophic factor: intranasal administration of femtomolar-acting peptides improve performance in a water maze. *J Pharmacol Exp Ther* 293:1091-1098.
9. Matsuoka, Y., Gray, A. J., Hirata-Fukae, C., Minami, S. S., Waterhouse, E. G., Mattson, M. P., LaFerla, F. M., Gozes, I., and Aisen, P. S. 2007. Intranasal NAP administration reduces accumulation of amyloid peptide and tau hyperphosphorylation in a transgenic mouse model of Alzheimer's disease at early pathological stage. *J Mol Neurosci* 31:165-170.
10. Matsuoka, Y., Jouroukhin, Y., Gray, A. J., Ma, L., Hirata-Fukae, C., Li, H. F., Feng, L., Lecanu, L., Walker, B. R., Planel, E., Arancio, O., Gozes, I., and Aisen, P. S. 2008. A neuronal microtubule-interacting agent, NAPVSIPQ, reduces tau pathology and enhances cognitive function in a mouse model of Alzheimer's disease. *J Pharmacol Exp Ther* 325:146-153.
11. Fleming, S. M., Mulligan, C. K., Richter, F., Mortazavi, F., Lemesre, V., Frias, C., Zhu, C., Stewart, A., Gozes, I., Morimoto, B., and Chesselet, M. F. 2011. A pilot trial of the microtubule-interacting peptide (NAP) in mice overexpressing alpha-synuclein shows improvement in motor function and reduction of alpha-synuclein inclusions. *Mol Cell Neurosci* 46:597-606.
12. Magen, I., Ostritsky, R., Richter, F., Zhu, C., Fleming, S. M., Lemesre, V., Stewart, A. J., Morimoto, B. H., Gozes, I., and Chesselet, M. F. 2014. Intranasal NAP (davunetide) decreases tau hyperphosphorylation and moderately improves behavioral deficits in mice overexpressing alpha-synuclein. *Pharmacol Res Perspect* 2:e00065.
13. Shiryaev, N., Jouroukhin, Y., Giladi, E., Polyzoidou, E., Grigoriadis, N. C., Rosenmann, H., and Gozes, I. 2009. NAP protects memory, increases soluble tau and reduces tau hyperphosphorylation in a tauopathy model. *Neurobiol Dis* 34:381-388.
14. Idan-Feldman, A., Schirer, Y., Polyzoidou, E., Touloumi, O., Lagoudaki, R., Grigoriadis, N. C., and Gozes, I. 2011. Davunetide (NAP) as a preventative treatment for central nervous system complications in a diabetes rat model. *Neurobiol Dis* 44:327-339.
15. Cash, A. D., Aliev, G., Siedlak, S. L., Nunomura, A., Fujioka, H., Zhu, X., Raina, A. K., Vinters, H. V., Tabaton, M., Johnson, A. B., Paula-Barbosa, M., Avila, J., Jones, P. K., Castellani, R. J., Smith, M. A., and Perry, G. 2003. Microtubule reduction in Alzheimer's disease and aging is independent of tau filament formation. *Am J Pathol* 162:1623-1627.

16. Merenlender-Wagner, A., Pikman, R., Giladi, E., Andrieux, A., and Gozes, I. 2010. NAP (davunetide) enhances cognitive behavior in the STOP heterozygous mouse—a microtubule-deficient model of schizophrenia. *Peptides* 31:1368-1373.
17. Merenlender-Wagner, A., Shemer, Z., Touloumi, O., Lagoudaki, R., Giladi, E., Andrieux, A., Grigoriadis, N. C., and Gozes, I. 2014. New horizons in schizophrenia treatment: autophagy protection is coupled with behavioral improvements in a mouse model of schizophrenia. *Autophagy* 10:2324-2332.
18. Vaisburd, S., Shemer, Z., Yeheskel, A., Giladi, E., and Gozes, I. 2015. Risperidone and NAP protect cognition and normalize gene expression in a schizophrenia mouse model. *Sci Rep* 5:16300.
19. Beni-Adani, L., Gozes, I., Cohen, Y., Assaf, Y., Steingart, R. A., Brenneman, D. E., Eizenberg, O., Trembolver, V., and Shohami, E. 2001. A peptide derived from activity-dependent neuroprotective protein (ADNP) ameliorates injury response in closed head injury in mice. *J Pharmacol Exp Ther* 296:57-63.
20. Romano, J., Beni-Adani, L., Nissenbaum, O. L., Brenneman, D. E., Shohami, E., and Gozes, I. 2002. A single administration of the peptide NAP induces long-term protective changes against the consequences of head injury: gene Atlas array analysis. *J Mol Neurosci* 18:37-45.
21. Leker, R. R., Teichner, A., Grigoriadis, N., Ovadia, H., Brenneman, D. E., Fridkin, M., Giladi, E., Romano, J., and Gozes, I. 2002. NAP, a femtomolar-acting peptide, protects the brain against ischemic injury by reducing apoptotic death. *Stroke* 33:1085-1092.
22. Zemlyak, I., Manley, N., Vulih-Shultzman, I., Cutler, A. B., Graber, K., Sapolsky, R. M., and Gozes, I. 2009. The microtubule interacting drug candidate NAP protects against kainic acid toxicity in a rat model of epilepsy. *J Neurochem* 111:1252-1263.
23. Spong, C. Y., Abebe, D. T., Gozes, I., Brenneman, D. E., and Hill, J. M. 2001. Prevention of fetal demise and growth restriction in a mouse model of fetal alcohol syndrome. *J Pharmacol Exp Ther* 297:774-779.
24. Zaltzman, R., Beni, S. M., Giladi, E., Pinhasov, A., Steingart, R. A., Romano, J., Shohami, E., and Gozes, I. 2003. Injections of the neuroprotective peptide NAP to newborn mice attenuate head-injury-related dysfunction in adults. *Neuroreport* 14:481-484.
25. Gozes, I., Stewart, A., Morimoto, B., Fox, A., Sutherland, K., and Schmechel, D. 2009. Addressing Alzheimer's disease tangles: from NAP to AL-108. *Curr Alzheimer Res* 6:455-460.
26. Morimoto, B. H., Schmechel, D., Hirman, J., Blackwell, A., Keith, J., and Gold, M. 2013. A double-blind, placebo-controlled, ascending-dose, randomized study to evaluate the safety, tolerability and effects on cognition of AL-108 after 12 weeks of intranasal administration in subjects with mild cognitive impairment. *Dement Geriatr Cogn Disord* 35:325-336.
27. Javitt, D. C., Buchanan, R. W., Keefe, R. S., Kern, R., McMahon, R. P., Green, M. F., Lieberman, J., Goff, D. C., Csernansky, J. G., McEvoy, J. P., Jarskog, F., Seidman, L. J., Gold, J. M., Kimhy, D., Nolan, K. S., Barch, D. S., Ball, M. P., Robinson, J., and Marder, S. R. 2012. Effect of the neuroprotective peptide davunetide (AL-108) on cognition and functional capacity in schizophrenia. *Schizophr Res* 136:25-31.
28. Jarskog, L. F., Dong, Z., Kangarlu, A., Colibazzi, T., Girgis, R. R., Kegeles, L. S., Barch, D. M., Buchanan, R. W., Csernansky, J. G., Goff, D. C., Harms, M. P., Javitt, D. C., Keefe, R. S., McEvoy, J. P., McMahon, R. P., Marder, S. R., Peterson, B. S., and Lieberman, J. A. 2013. Effects of davunetide on N-acetylaspartate and choline in dorsolateral prefrontal cortex in patients with schizophrenia. *Neuropsychopharmacology* 38:1245-1252.
29. Boxer, A. L., Lang, A. E., Grossman, M., Knopman, D. S., Miller, B. L., Schneider, L. S., Doody, R. S., Lees, A., Golbe, L. I., Williams, D. R., Corvol, J. C., Ludolph, A., Burn, D., Lorenzl, S., Litvan, I., Roberson, E. D., Hoglinger, G. U., Koestler, M., Jack, C. R., Jr., Van Deerlin, V., Randolph, C., Lobach, I. V., Heuer, H. W., Gozes, I., Parker, L., Whitaker, S., Hirman, J., Stewart, A. J., Gold, M., Morimoto, B. H., and Investigators, A. L. 2014. Davunetide in patients with progressive supranuclear palsy: a randomised, double-blind, placebo-controlled phase 2/3 trial. *Lancet Neurol* 13:676-685.
30. Alcalay, R. N., Giladi, E., Pick, C. G., and Gozes, I. 2004. Intranasal administration of NAP, a neuroprotective peptide, decreases anxiety-like behavior in aging mice in the elevated plus maze. *Neurosci Lett* 361:128-131.
31. Gozes, I., Morimoto, B. H., Tiong, J., Fox, A., Sutherland, K., Dangoor, D., Holser-Cochav, M., Vered, K., Newton, P., Aisen, P. S., Matsuoka, Y., van Dyck, C. H., and Thal, L. 2005. NAP: research and development of a peptide derived from activity-dependent neuroprotective protein (ADNP). *CNS Drug Rev* 11:353-368.
32. Morimoto, B. H., de Lannoy, I., Fox, A. W., Gozes, I., and Stewart, A. J. 2009. Davunetide: Pharmacokinetics and distribution to brain after intravenous or intranasal administration to rat. *chimica Oggi/CHEMISTRY today* 27:16-20.
33. Morimoto, B. H., Fox, A. W., Stewart, A. J., and Gold, M. 2013. Davunetide: a review of safety and efficacy data with a focus on neurodegenerative diseases. *Expert Rev Clin Pharmacol* 6:483-502.
34. Pinhasov, A., Mandel, S., Torchinsky, A., Giladi, E., Pittel, Z., Goldsweig, A. M., Servoss, S. J., Brenneman, D. E., and Gozes, I. 2003. Activity-dependent neuroprotective protein: a novel gene essential for brain formation. *Brain Res Dev Brain Res* 144:83-90.
35. Vulih-Shultzman, I., Pinhasov, A., Mandel, S., Grigoriadis, N., Touloumi, O., Pittel, Z., and Gozes, I. 2007. Activity-dependent neuroprotective protein snippet NAP reduces tau hyperphosphorylation and enhances learning in a novel transgenic mouse model. *J Pharmacol Exp Ther* 323:438-449.
36. Shiryaev, N., Pickman, R., Giladi, E., and Gozes, I. 2011. Protection against tauopathy by the drug candidates NAP (Davunetide) and D-SAL: Biochemical, cellular and behavioral aspects. *Curr Pharm Design* 17:2603-2612.
37. Malishkevich, A., Amram, N., Hacohen-Kleiman, G., Magen, I., Giladi, E., and Gozes, I. 2015. Activity-dependent neuroprotective protein (ADNP) exhibits striking sexual dichotomy impacting on autistic and Alzheimer's pathologies. *Transl Psychiatry* 5:e501.
38. Helsmoortel, C., Vulto-van Silfhout, A. T., Coe, B. P., Vandeweyer, G., Rooms, L., van den Ende, J., Schuurs-Hoeijmakers, J. H., Marcelis, C. L., Willemsen, M. H., Vissers, L. E., Yntema, H. G., Bakshi, M., Wilson, M., Witherspoon, K. T., Malmgren, H., Nordgren, A., Anneren, G., Fichera, M., Bosco, P., Romano, C., de Vries, B. B., Kleefstra, T., Kooy, R. F., Eichler, E. E., and Van der Aa, N. 2014. A SWI/SNF-related autism syndrome caused by de novo mutations in ADNP. *Nat Genet* 46:380-384.

39. Gozes, I., Helsmoortel, C., Vandeweyer, G., Van der Aa, N., Kooy, F., and Sermone, S. B. 2015. The Compassionate Side of Neuroscience: Tony Sermone's Undiagnosed Genetic Journey-ADNP Mutation. *J Mol Neurosci* 56:751-757.
40. Dresner, E., Agam, G., and Gozes, I. 2011. Activity-dependent neuroprotective protein (ADNP) expression level is correlated with the expression of the sister protein ADNP2: deregulation in schizophrenia. *Eur Neuropsychopharmacol* 21:355-361.
41. Malishkevich, A., Marshall, G. A., Schultz, A. P., Sperling, R. A., Aharon-Peretz, J., and Gozes, I. 2015. Blood-Borne Activity-Dependent Neuroprotective Protein (ADNP) is Correlated with Premorbid Intelligence, Clinical Stage, and Alzheimer's Disease Biomarkers. *J Alzheimers Dis*.
42. Huang, J. P., Cui, S. S., Han, Y., Irva, H. P., Qi, L. H., and Zhang, X. 2014. Prevalence and Early Signs of Autism Spectrum Disorder (ASD) among 18-36 Month Old Children in Tianjin of China. *Biomed Environ Sci* 27:453-461.
43. Liu, X., Bipolar Genome, S., Kelsoe, J. R., and Greenwood, T. A. 2016. A genome-wide association study of bipolar disorder with comorbid eating disorder replicates the SOX2-OT region. *J Affect Disord* 189:141-149.
44. Mandel, S., and Gozes, I. 2007. Activity-dependent neuroprotective protein constitutes a novel element in the SWI/SNF chromatin remodeling complex. *J Biol Chem* 282:34448-34456.
45. Mandel, S., Rechavi, G., and Gozes, I. 2007. Activity-dependent neuroprotective protein (ADNP) differentially interacts with chromatin to regulate genes essential for embryogenesis. *Dev Biol* 303:814-824.
46. Gulsuner, S., Walsh, T., Watts, A. C., Lee, M. K., Thornton, A. M., Casadei, S., Rippey, C., Shahin, H., Consortium on the Genetics of, S., Group, P. S., Nimgaonkar, V. L., Go, R. C., Savage, R. M., Swerdlow, N. R., Gur, R. E., Braff, D. L., King, M. C., and McClellan, J. M. 2013. Spatial and temporal mapping of de novo mutations in schizophrenia to a fetal prefrontal cortical network. *Cell* 154:518-529.
47. Brenneman, D. E., Hauser, J., Phillips, T. M., Davidson, A., Bassan, M., and Gozes, I. 1999. Vasoactive intestinal peptide. Link between electrical activity and glia-mediated neurotrophism. *Ann N Y Acad Sci* 897:17-26.
48. Costantino, H. R., Culley, H., Chen, L., Morris, D., Houston, M., Roth, S., Phoenix, M. J., Foerder, C., Philo, J. S., Arakawa, T., Eidenschink, L., Andersen, N. H., Brandt, G., and Quay, S. C. 2009. Development of Calcitonin Salmon Nasal Spray: similarity of peptide formulated in chlorobutanol compared to benzalkonium chloride as preservative. *J Pharm Sci* 98:3691-3706.
49. Rotstein, M., Bassan, H., Kariv, N., Speiser, Z., Harel, S., and Gozes, I. 2006. NAP enhances neurodevelopment of newborn apolipoprotein E-deficient mice subjected to hypoxia. *J Pharmacol Exp Ther* 319:332-339.
50. Stein, L. I., Lane, C. J., Williams, M. E., Dawson, M. E., Polido, J. C., and Cermak, S. A. 2014. Physiological and behavioral stress and anxiety in children with autism spectrum disorders during routine oral care. *Biomed Res Int* 2014:694876.
51. Lepp, S., Anderson, A., and Konopka, G. 2013. Connecting signaling pathways underlying communication to ASD vulnerability. *Int Rev Neurobiol* 113:97-133.
52. Spencer, C. M., Alekseyenko, O., Hamilton, S. M., Thomas, A. M., Serysheva, E., Yuva-Paylor, L. A., and Paylor, R. 2011. Modifying behavioral phenotypes in Fmr1 KO mice: genetic background differences reveal autistic-like responses. *Autism Res* 4:40-56.
53. Shu, W., Cho, J. Y., Jiang, Y., Zhang, M., Weisz, D., Elder, G. A., Schmeidler, J., De Gasperi, R., Sosa, M. A., Rabidou, D., Santucci, A. C., Perl, D., Morrisey, E., and Buxbaum, J. D. 2005. Altered ultrasonic vocalization in mice with a disruption in the Foxp2 gene. *Proc Natl Acad Sci USA* 102:9643-9648.
54. Noirot, E. a. P., D. 1969. Sound analysis of ultrasonic distress calls of mouse pups as a function of their age. *Animal Behaviour* Volume 17, Part 2:340-349.
55. Gozes, I., Sragovich, S., Schirer, Y., and Idan-Feldman, A. 2016. D-SAL and NAP: Two Peptides Sharing a SIP Domain. *J Mol Neurosci* In Press.
56. Malishkevich, A., Leyk, J., Goldbaum, O., Richter-Landsberg, C., and Gozes, I. 2015. ADNP/ADNP2 expression in oligodendrocytes: implication for myelin-related neurodevelopment. *J Mol Neurosci* 57:304-313.
57. Pescosolido, M. F., Schwede, M., Johnson Harrison, A., Schmidt, M., Gamsiz, E. D., Chen, W. S., Donahue, J. P., Shur, N., Jerskey, B. A., Phornphutkul, C., and Morrow, E. M. 2014. Expansion of the clinical phenotype associated with mutations in activity-dependent neuroprotective protein. *J Med Genet* 51:587-589.
58. Millar, J. K., Christie, S., and Porteous, D. J. 2003. Yeast two-hybrid screens implicate DISC1 in brain development and function. *Biochem Biophys Res Commun* 311:1019-1025.
59. Walker, R. M., Hill, A. E., Newman, A. C., Hamilton, G., Torrance, H. S., Anderson, S. M., Ogawa, F., Derizioti, P., Nicod, J., Vernes, S. C., Fisher, S. E., Thomson, P. A., Porteous, D. J., and Evans, K. L. 2012. The DISCI promoter: characterization and regulation by FOXP2. *Hum Mol Genet* 21:2862-2872.
60. Lai, C. S. L., Fisher, S. E., Hurst, J. A., Vargha-Khadem, F., and Monaco, A. P. 2001. A forkhead-domain gene is mutated in a severe speech and language disorder. *Nature* 413:519-523.
61. MacDermot, K. D., Bonora, E., Sykes, N., Coupe, A.-M., Lai, C. S. L., Vernes, S. C., Vargha-Khadem, F., McKenzie, F., Smith, R. L., Monaco, A. P., and Fisher, S. E. 2005. Identification of FOXP2 Truncation as a Novel Cause of Developmental Speech and Language Deficits. *The American Journal of Human Genetics* 76:1074-1080.
62. Sanjuan, J., Tolosa, A., Gonzalez, J. C., Aguilar, E. J., Molto, M. D., Najera, C., and de Frutos, R. 2005. FOXP2 polymorphisms in patients with schizophrenia. *Schizophr Res* 73:253-256.
63. Sanjuan, J., Tolosa, A., Gonzalez, J. C., Aguilar, E. J., Perez-Tur, J., Najera, C., Molto, M. D., and de Frutos, R. 2006. Association between FOXP2 polymorphisms and schizophrenia with auditory hallucinations. *Psychiatr Genet* 16:67-72.
64. Tolosa, A., Sanjuan, J., Dagnall, A. M., Molto, M. D., Herrero, N., and de Frutos, R. 2010. FOXP2 gene and language impairment in schizophrenia: association and epigenetic studies. *BMC Med Genet* 11:114.
65. Li, T., Zeng, Z., Zhao, Q., Wang, T., Huang, K., Li, J., Li, Y., Liu, J., Wei, Z., Wang, Y., Feng, G., He, L., and Shi, Y. 2013. FoxP2 is significantly associated with schizophrenia and major depression in the Chinese Han population. *World J Biol Psychiatry* 14:146-150.
66. Marcus, G. F., and Fisher, S. E. 2003. FOXP2 in focus: what can genes tell us about speech and language? *Trends Cogn Sci* 7:257-262.

67. Belokopytov, M., Shulman, S., Dubinsky, G., Gozes, I., Belkin, M., and Rosner, M. 2011. Ameliorative effect of NAP on laser-induced retinal damage. *Acta Ophthalmol* 89:e126-131.
68. Jehle, T., Dimitriu, C., Auer, S., Knoth, R., Vidal-Sanz, M., Gozes, I., and Lagreze, W. A. 2008. The neuropeptide NAP provides neuroprotection against retinal ganglion cell damage after retinal ischemia and optic nerve crush. *Graefes Arch Clin Exp Ophthalmol* 246:1255-1263.
69. Lagreze, W. A., Pielen, A., Steingart, R., Schlunck, G., Hofmann, H. D., Gozes, I., and Kirsch, M. 2005. The peptides ADNF-9 and NAP increase survival and neurite outgrowth of rat retinal ganglion cells in vitro. *Invest Ophthalmol Vis Sci* 46:933-938.
70. Gobbels, M., and Spitznas, M. 1989. Influence of artificial tears on corneal epithelium in dry-eye syndrome. *Graefes Arch Clin Exp Ophthalmol* 227:139-141.
71. Heimesaat, M. M., Fischer, A., Kuhl, A. A., Gobel, U. B., Gozes, I., and Bereswill, S. 2015. Anti-Inflammatory Properties of NAP in Acute Toxoplasma Gondii-Induced Ileitis in Mice. *Eur J Microbiol Immunol* (Bp) 5:210-220.

What is claimed is:

1. A method for treating a patient affected by an activity-dependent neuroprotective protein (ADNP) mutation, comprising:
   (i) selecting a male patient with an ADNP mutation; and
   (ii) administering to the patient a composition comprising an effective amount of an NAP peptide (NAPVSIPQ, SEQ ID NO:1) and benzalkonium chloride, thereby improving arm muscle strength in the patient.

2. The method of claim 1, wherein the patient is a child.

3. The method of claim 1, wherein the patient is diagnosed with or at risk of developing schizophrenia.

4. The method of claim 1, wherein the patient is diagnosed with or at risk of developing autism.

5. The method of claim 1, wherein the patient is diagnosed with or at risk of developing cognitive impairment.

6. The method of claim 1, wherein the patient is diagnosed with or at risk of developing motor disabilities.

7. The method of claim 1, wherein the composition further comprises chlorobutanol.

8. The method of claim 1, wherein the composition comprises an NAP peptide (NAPVSIPQ, SEQ ID NO:1) at the concentration of about 1-250 mg/ml, chlorobutanol at the concentration of about 0.25%, about 0.85% NaCl, and has a pH of about 3.5.

9. The method of claim 1, wherein the composition further comprises an anti-psychotic agent.

10. The method of claim 1, wherein the administering is via nasal administration.

11. The method of claim 1, wherein the administering is performed once or twice every day.

12. The method of claim 1, wherein the administering is performed for a time period of 2 weeks, 1 month, 6 months, 1 year, 5 years, 10 years, or 20 years or longer.

13. The method of claim 1, wherein the composition comprises 7.5 mg/ml of NaCl, 1.7 mg/ml of citric acid, 3 mg/ml of disodium phosphate dihydrate, and 0.2 mg/ml of 50% benzalkonium chloride solution.

* * * * *

SEQUENCE LISTING

```
<160> NUMBER OF SEQ ID NOS: 7

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Asn Ala Pro Val Ser Ile Pro Gln
1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Lys Ile Pro
1

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ser Ala Leu Leu Arg Ser Ile Pro Ala
1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Asn Ala Val Ser Ile Gln
1               5

<210> SEQ ID NO 5
<211> LENGTH: 8
<212> TYPE: PRT
<213> ORGANISM: Artificial Sequence
<220> FEATURE:
<223> OTHER INFORMATION: Description of Artificial Sequence: Synthetic
```

```
                            peptide

<400> SEQUENCE: 5

Asn Ala Pro Val Ser Leu Ser Gln
1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Asn Thr Pro Val Ser Leu Ser Gln
1               5

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Lys Lys Tyr Leu
1
```